United States Patent [19]
Krenitsky et al.

[11] Patent Number: 5,747,472
[45] Date of Patent: *May 5, 1998

[54] THERAPEUTIC METHODS FOR USING ARA-G DERIVATIVES

[75] Inventors: Thomas Anthony Krenitsky, Chapel Hill; Devron Randolph Averett, Raleigh; George Walter Koszalka, Chapel Hill; Gerald Wolberg, Cary, all of N.C.

[73] Assignee: Glaxo Wellcome Inc., Research Triangle Park, N.C.

[ * ] Notice: The term of this patent shall not extend beyond the expiration date of Pat. No. 5,492,897.

[21] Appl. No.: 456,186

[22] Filed: May 31, 1995

Related U.S. Application Data

[60] Continuation of Ser. No. 224,343, Apr. 7, 1994, Pat. No. 5,492,897, which is a division of Ser. No. 731,969, Jul. 18, 1991, abandoned.

[30] Foreign Application Priority Data

Jul. 19, 1990 [GB] United Kingdom ............... 9015914

[51] Int. Cl.$^6$ .................................. A61K 32/70
[52] U.S. Cl. ............... 514/45; 514/46; 514/814; 514/883; 514/908; 536/27.4
[58] Field of Search ............... 514/45, 46, 814, 514/883, 908; 536/27.4

[56] References Cited

U.S. PATENT DOCUMENTS

| | | | |
|---|---|---|---|
| 4,081,534 | 3/1978 | Elion et al. | 514/45 |
| 5,352,669 | 10/1994 | Moschel et al. | 514/45 |
| 5,424,295 | 6/1995 | Krenitsky et al. | 514/45 |
| 5,492,897 | 2/1996 | Krenitsky et al. | 514/45 |

*Primary Examiner*—James O. Wilson
*Attorney, Agent, or Firm*—Karen L. Prus; George W. Neuner

[57] ABSTRACT

6-Alkoxy derivatives of Ara-G, and pharmaceutically acceptable esters thereof, are described as being useful in tumour therapy. Novel pharmaceutically acceptable esters, their preparation and pharmaceutical formulations containing them are also disclosed.

11 Claims, No Drawings

THERAPEUTIC METHODS FOR USING ARA-G DERIVATIVES

This is a continuation of applications Ser. No. 08/224,343 filed on Apr. 7, 1994, now U.S. Pat. No. 5,492,897, which is a divisional of U.S. Ser. No. 07/731,969 filed Jul. 18, 1991, now abandoned.

The present invention relates to the antitumour and immunomodulatory activities of certain arabinofuranosyl purine derivatives.

It has been reported (Blood, 61, (1983), 660; J. Clin. Invest., 74, (1984), 951 and Cancer Research, 45, (1985), 1008) that arabinofuranosyl guanine (ara G) selectively inhibits the growth of T cells compared to B cells and possesses a selective cytotoxic activity for T-leukemic cells. Ara G has been proposed as a putative chemotherapeutic or immunosuppressive agent.

European Patent Application No. 294 114 discloses purine arabinosides and pharmaceutically acceptable derivatives thereof for the treatment of human viral infection caused by certain herpes viruses.

It has now been discovered that compounds of formula (I)

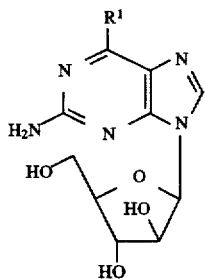

wherein $R^1$ is a $C_{1-5}$ alkoxy group and pharmaceutically acceptable esters thereof are useful antitumour agents, and, in particular, are useful in the treatment of T-cell lymphoproliferative disorders in mammals, e.g., humans. Thus they are useful for the treatment of lymphocytic leukemia, malignant lymphoma, autoimmune diseases (e.g. rheumatoid arthritis, multiple sclerosis, systemic lupus erythematosus and type 1, or insulin-dependent, diabetes mellitus) and as immunomodulators.

Accordingly, the present invention provides the use of a compound of formula (I) wherein $R^1$ is a $C_{1-5}$ alkoxy group, or a pharmaceutically acceptable ester thereof, in the manufacture of a medicament for antitumour therapy.

In a further aspect, the present invention provides a method for the inhibition of tumours in mammals which comprises administering to the mammal an effective amount of a compound of formula (I) wherein $R^1$ is a $C_{1-5}$ alkoxy group or a pharmaceutically acceptable ester thereof.

Suitably $R^1$ is methoxy or ethoxy and preferably a methoxy group.

In a further aspect, the present invention provides novel pharmaceutically acceptable esters of compounds of the formula (I) wherein $R^1$ is a $C_{1-5}$ alkoxy group.

The pharmaceutically acceptable esters of the above compounds of formula (I) are particularly preferred since they are capable of providing high levels of ara G in the plasma of a subject after oral administration.

It has been discovered that compounds of the invention are enzymatically converted to ara G in the host. Since ara G has limited water solubility making parenteral administration impractical, as well as giving low bioavailability after oral dosing in primates, the use of a compound of the invention is advantageous for treatment of the above mentioned disorders and diseases.

Preferred derivatives of compounds of the invention include mono- di- or tri-esters of the arabino-sugar residue substituted at the 2'-, 3'- and 5'-positions of said residue.

Such preferred esters include carboxylic acid esters in which the non-carbonyl moiety of the ester grouping is selected from straight or branched chain alkyl (e.g. n-propyl, c-butyl, n-butyl), alkoxyalkyl (e.g. methoxymethyl), aralkyl (e.g. benzyl), aryloxyalkyl (e.g. phenoxymethyl), aryl (e.g. phenyl) optionally substituted by halogen, $C_{1-4}$ alkyl or $C_{1-4}$ alkoxy, nitro or amino; sulphonate esters such as alkylsulphonyl; or alkylarylsulphonyl (e.g. methanesulphonyl or tosylsulphonyl); dicarboxylic acid esters (e.g. succinyl) or $C_{1-4}$ alkyl esters thereof; amino acid esters (e.g. L-valyl); and mono-, di- or tri-phosphate esters. Pharmaceutically acceptable salts of these esters include sodium, potassium, $NR_4^+$ where R—H or $C_{1-6}$ alkyl, halides and acid addition salts. In the above ester groups, the alkyl groups (including those in alkoxy groupings) contain 1 to 12 carbon atoms and the aryl groups are preferably phenyl.

Preferred esters of the present invention include:
1) 2-Amino-6-methoxy-9-(5-O-propionyl-β-D-arabinofuranosyl)-9H-purine.
2) 2-Amino-9-(5-O-butyryl-β-D-arabinofuranosyl)-6-methoxy-9H-purine.
3) 2-Amino-6-methoxy-9-(3-O-pivaloyl-β-D-arabinofuranosyl)-9H-purine.
4) 2-Amino-6-methoxy-9-(2-O-valeryl-β-D-arabinofuranosyl)-9H-purine.
5) 2-Amino-9-(3-O-benzoyl-β-D-arabinofuranosyl)-6-methoxy-9H-purine.
6) 2-Amino-6-methoxy-9-(2-O-pivaloyl-β-D-arabinofuranosyl)-9H-purine.
7) 2-Amino-9-(2-O-benzoyl-β-D-arabinofuranosyl)-6-methoxy-9H-purine.
8) 2-Amino-6-methoxy-9-(5-O-valeryl-β-D-arabinofuranosyl)-9H-purine.
9) (5-O-Acetyl-β-D-arabinofuranosyl)-2-amino-6-methoxy-9-9H-purine.
10) 2-Amino-6-methoxy-9-(5-O-(4-methoxy-4-oxobutyryl)-β-D-arabinofuranosyl)-9H-purine.
11) 9-(3,5-di-O-Acetyl-β-D-arabinofuranosyl)-2-amino-6-methoxy-9H-purine.
12) 9-(2,5-di-O-Acetyl-β-D-arabinofuranosyl)-2-amino-6-methoxy-9H-purine.
13) 9-(2-O-Acetyl-β-D-arabinofuranosyl)-2-amino-6-methoxy-9H-purine.
14) 9-(2,3,5-tri-O-Acetyl-β-D-arabinofuranosyl)-2-amino-6-methoxy-9H-purine
15) 2-Amino-9-(5-O-isobutyryl-β-D-arabinofuranosyl)-6-methoxy-9H-purine
16) 9-(2,3-di-O-Acetyl-β-D-arabinofuranosyl)-2-amino-6-methoxy-9H-purine The 3,5-di-O-acetyl ester (compound 11), the 5-O-(4-methoxy-4-oxobutyryl) ester (compound 10) and the 5-O-acetyl ester, (compound 9), are especially preferred esters.

The compounds of the present invention are efficient prodrugs of ara G, a selective inhibitor of T-cell growth. The present invention provides therefore a method for inhibiting the replication and/or functions of T-cells by the administration of an effective amount of a compound of the present invention.

Treatment of neoplastic growth with a compound of the present invention may involve the administration of the compound alone or in combination with other drugs as a preparatory regimen intended to cause bone marrow ablation prior to autologous or allogeneic bone marrow transplantation for leukemia, lymphoma, myeloma or other malignancies, for example in an analogous manner to the administration of high doses of busulfan and cyclophosphamide prior to bone marrow transplantation for acute leukemia. (Santos, G. W., Bone Marrow Transplant, 1989 January 4 suppl. 1, 236–9).

A compound of the present invention may also be used to treat blood or bone marrow ex vivo to remove malignant stem cells, in an analogous manner to that described for 4-hydroperoxycyclophosphamide by Yeager, A. M. et al., N. Engl. J. Med., Jul. 17 1986, 315 (3), 141–7.

T-cells are found in rheumatoid joints and may contribute to the inflammatory process. About 1% of all populations (women 2 to 3 times more commonly than men) are affected by rheumatoid arthritis, and 5 to 10% of rheumatoid arthritis patients are eventually disabled by painful, swollen joints despite full treatment. A compound of the present invention may be used to treat rheumatoid arthritis.

It has also been postulated that T-cells play a role in muscular dystrophy; the present invention provides therefore for the use of a compound of the present invention in the treatment of muscular dystrophy.

The compounds of formula (I) wherein $R^1$ is a $C_{1-5}$ alkoxy group and pharmaceutically acceptable esters thereof (hereafter collectively referred to as the active ingredients) may be administered by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

For each of the above-indicated disorders, diseases and indications, the amount required of an active ingredient (as above defined) will depend upon a number of factors, including the severity of the condition to be treated and the identity of the recipient and will ultimately be at the discretion of the attendant physician. In general, however, for each of these utilities and indications, a suitable, effective dose will be in the range 0.1 to 250 mg per kilogram body weight of recipient per day, preferably in the range 0.1 to 100 mg per kilogram body weight per day and most preferably in the range 1 to 20 mg per kilogram body weight per day; an optimum dose is between 5 and 15 mg per kilogram body weight per day (unless otherwise indicated all weights of active ingredient are calculated as the parent compound of formula (I); for salts and esters thereof the figures would be increased proportionately). The desired dose is preferably presented as one, two, three, four or more sub-doses administered at appropriate intervals throughout the day or week. These sub-doses may be administered in unit dosage forms, for example, containing 5 to 1000 mg, preferably 20 to 500 mg and most preferably 100 to 400 mg of active ingredient per unit dosage form.

It will be appreciated that processes which affect T-cell function, such as required for treatment of autoimmune diseases (e.g. rheumatoid arthritis) would generally be at the lower end of the above dose ranges.

While it is possible for the active ingredients to be administered alone it is preferable to present them as pharmaceutical formulations. The formulations of the present invention comprise at least one active ingredient, as above defined, together with one or more acceptable carriers thereof, and optionally other therapeutic ingredients. The carrier(s) must be "acceptable" in the sense of being compatible with the other ingredients of the formulation and not deleterious to the recipients thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compression tablets may be prepared by compressing in an suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide the desired release profile.

For treatment of external tissues, e.g., mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream may include, for example, at least 30% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with an lipophilic emulsifier which acts as a stabilizer. It is also preferred to include both an oil and a fat. Together, the emulsifier(s) with or without stabilizers make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono-or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration in the mouth include lozenges comprising the active ingredient in a flavoured base, usually sucrose and acacia or tragacanth; pastilles comprising the active ingredient in an inert base such as gelatin and glycerin, or sucrose and acacia; and mouth-washes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a weekly dose, a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The present invention also provides a process for the preparation of a pharmaceutically acceptable ester of a compound of formula (I) wherein $R^1$ is a $C_{1-5}$ alkoxy group, comprising the esterification of a compound of the formula (I). Such esterification may take place by the reaction of a compound of the formula (I), in which the non-protected hydroxy groups are esterified with an acylating agent, conveniently an acyl halide or anhydride, at a non-extreme temperature, $-30°$ C. to $100°$ C. and suitably $-5°$ to $30°$ C., in a polar solvent, conveniently acetonitrile, in the presence of a base, for example triethylamine, and then removing the protecting groups by conventional means.

Alternatively, the esters may be prepared by enzymatic esterification for example using the appropriate trichloroethyl ester and subtilisin as the reaction initiator. The reaction is suitably carried out in a basic solvent, such as pyridine at a non-extreme temperature, conveniently between $10°$ C. and $50°$ C. The reaction is quenched by filtering off the enzyme and removing the solvent.

The compounds of the formula (I) may be prepared by the method described in European Patent Application No. 294114 (when $R^1$ is $C_{1-5}$ alkoxy).

The following examples serve to illustrate the preparation of esters of compounds of the formula (I) and formulations containing them.

EXAMPLE 1

Enzymatic Preparation of Esters of the Present Invention a) 2-Amino-6-methoxy-9-(5-O-propionyl-β-D-arabinofuranosyl)-9H-purine 2-Amino-6-methoxy-9-(β-D-arabinofuranosyl)-9H-purine (1.0 g, 3.3 mmol) (prepared as described in European Patent Application No. 294 114) was suspended in 40 ml of pyridine that contained 300 µL of $H_2O$ and 2 ml of trichloroethyl propionate (Trichloroethyl propionate was synthesized by addition of 19 ml of propionyl chloride (Aldrich) over 30 minutes to 19.1 ml of trichlorethanol (Aldrich) in 40 ml of pyridine at $0°$ C.). The product was purified by successive washing with 2×100 ml aliquots of $H_2O$, 5% $NaHCO_3$, and $H_2O$. $^1$H NMR (200 MHz, $CDCl_3$, 4.74 (s, 2H, $Cl_3CH_2$), 2.49 (q, 2H, J=7.6 Hz, $CH_3CH_2CO_2$), 1.21 (t, 3H, J=7.6 Hz, $CH_3CH_2CO_2$). The reaction was initiated with 0.100 g of subtilisin (Sigma Chemical Co., St. Louis, Mo., P-5380, lot No. 38F-0356), whch had been activated by dissolving 1 g of the enzyme in 20 ml of 0.1M potassium phosphate at pH 7.8 and lyophilizing to dryness. After stirring for 23 hours at $40°$ C., the reaction was quenched by filtering off the enzyme and the solvent was removed in vacuo. The crude product was purified by chromatography on a 4.5×25 cm silica gel column with $CH_2Cl_2:CH_3OH$ (9:1) as eluant. Product fractions were pooled and lyophilized from water to yield 0.76 g of the desired product as a white powder: m.p. $124°$ C.; TLC $R_f$=0.43 (silica gel; $CH_1Cl_2:CH_3OH$ (9:1)); UV λmax (ε, $mM^{-1}$ $cm^{-1}$) at pH 7.0, 278 nm (9.5). $^1$H NMR (200 MHz, DMSO-$d_6$), δ 7.83(s, 1H, $H_8$, 6.44 (s, 2H, 2-$NH_2$), 6.14 (s, 1H, $H_{1'}$), 5.75 (d, 1H, J=4.3 Hz, 2'-OH), 5.65 (d, 1H, J=3.5 Hz, 3'-OH), 4.28 (m, 2H, $H_{2'}$ and $H_{3'}$), 4.08 (m, 2H, $H_5$), 3.95 (s, 3H, —$OCH_3$), 3.91 (m, 1H, $H_{4'}$), 2.32 (q, 2H, J=7.6 Hz, $CH_3CH_2CO_2$), 1.01 (t, 3H, J=7.5 Hz, $\underline{C}H_3CH_2CO_2$); MS (ci) 354 (M+1), 280 (M—$C_2H_5$ $CO_2$). Anal. Calcd. for $C_{14}H_{19}N_5O_6$.0.46 $H_2O$: Calcd: C, 46.49; H, 5.55; N, 19.36 Found: C, 46.46; H, 5.52; N, 19.45.

b) 9-(5-O-Acetyl-β-D-arabinofuranosyl)-2-amino-6-methoxy-9H-purine

2-Amino-6-methoxy-9-β-D-arabinofuranosyl-9H-purine (1.0 g, 3.3 mmol) was suspended in 40 ml of pyridine that contained 300 μL of $H_2O$ and 1 ml of trichloroethyl acetate (Trichloroethyl acetate was synthesized as follows: 2,2,2-trichloroethanol (19.1 mL, 197.1 mmole) and dry pyridine (40 mL) were placed in a three-neck, round-bottom flask equipped with argon inlet valve, thermometer, dropping funnel, magnetic stirring, and ice/$H_2O$ bath. Acetyl chloride (14.5 mL), 199.8 mmole) was placed in the dropping funnel and added over a ten minute period, keeping the temperature below 25° C. while stirring under argon. The resulting product was washed with $H_2O$ (2×100 mL), 5% $NaHCO_3$ (2×100 mL), and $H_2O$ (2×100 mL). The organic layer was dried over $MgSO_4$ then filtered through Whatman No. 1 paper, and distilled under vacuum. A middle cut of 5.18 g was the desired material, contaminated with a small amount of acetic acid.

$^1$H-NMR (CDCl$_3$): δ 4.73 (s, 2H, $CH_2O$ ), 2.20 (s, 3H, $CH_3CO$); MS CI, $CH_4$): m/z 197 (M+H, $C_4H_5O_2{}^{37}Cl_3$), 195 (M+H, $C_4H_5O_2{}^{37}Cl_2{}^{35}Cl$), 193 (M+H, $C_4H_5O_2O^{35}Cl_2{}^{37}Cl$), 191 (M+H, $C_4H_5O_2{}^{35}Cl_3$), 159 (195-HCl, $C_4H_4O_2{}^{37}Cl_2$), 157 (193-HCl, $C_4H_4O_2{}^{37}Cl^{35}Cl$), 155 (191-HCl, $C_4H_4O_2{}^{35}Cl_2$); (EI): m/z 195 (M+H), 193 (M+H), 191 (M+H), 157 (193-HCl ), 155 (191-HCl ). Analysis for $C_4H_5Cl_3O_2$+0.054 mole $CH_3COOH$: C, 25.35; H, 2.70; Cl, 54.62. Found: C, 25.57; H, 2.72; Cl, 54.66).

The reaction was initiated with 0.050 g of subtilisin (Sigma Chemical Co., St. Louis, Mo., P-5380, Lot No. 38F-0356), which had been activated by dissolving 1 g of the enzyme in 20 ml of 0.1M potassium phosphate at pH 7.8 and lyophilizing to dryness. After stirring for 23 hours ac 40° C. an additional 50 mg of subtilisin and 2 ml of trichloroethyl acetate were added to the reaction. After stirring at 40° C. for an additional 24 hours the reaction was quenched by filtering off the enzyme and the solvent was removed in vacuo. The crude product was purified by chromatography on a 4.5×25 cm silica gel column with $CH_2Cl_2$:$CH_3OH$ (9:1) as eluant. Product fractions were pooled and lyophilized from water to yield 0.28 g of the desired product as a white powder. TLC $R_f$=0.35 (silica gel; $CH_2Cl_2$:$CH_3OH$ (9:1)); UV $\lambda_{max}$ (ε, $mM^{-1}$ $cm^{-1}$) at pH 7.0, 279 nm (8.8). $^1$H-NMR (200 MHz, DMSO-d$_6$): δ 7.83 (s, 1H, H$_8$), 6.45 (s, 2H, 2-NH$_2$), 6.14 (d, 1H, J=3.7 Hz, H$_{1'}$), 5.75 (d, 1H, J=4.5 Hz, 2'-OH), 5.65 (d, 1H, J=3.7 Hz, 3'-OH), 4.26 (m, 2H, H$_{2'}$ and H$_{3'}$), 4.07 (m, 2H, H$_{5'}$) 3.94 (s, 3H, —OCH$_3$) 3.92 (m, 1H, H$_{4'}$), 2.01 (s, 3H, CH$_3$CO$_2$-); MS (CI) 340 (M+1), 280 (M—CH$_3$CO$_2$). Anal. Calcd. for $C_{13}H_{17}N_5O_6$·0.52 $H_2O$: Calcd: C, 44.77; H, 5.22; N, 20.12. Found: C, 44.79; H, 5.21; N, 20.09.

The following compounds were prepared in an analogous manner starting from the appropriate trichloroethyl ester c) 2-Amino-9-(5-O-Butyryl-β-D-arabinofuranosyl)-6-methoxy-9H-purine $^1$H NMR (200 MHz, DMSO-d$_6$): δ 7.83 (s, 1H, H$_8$), 6.46 (s, 2H, 2-NH$_2$), 6.14 (d, 1H, J=3.9 Hz, H1'), 5.76 (d, 1H, J=4.3 Hz, 2'-OH), 5.66 (D, 1H, J=3.7 Hz, 3'-OH), 4.28 (m, 2H, H$_{2'}$ and H$_{3'}$), 4.07 (m, 2H, H$_{5'}$), 3.94 (s, 3H, —OCH$_3$), 3.91 (m, 1H, H$_{4'}$), 2.28 (t, 2H, J=7.2 Hz, CH$_3$CH$_2$CH$_2$CO$_2$-), 1.52 (sextet, 2H, J=7.4 Hz, CH$_3$CH$_2$CH$_2$CO$_2$-), 0.85 (t, 3H, J=7.3 Hz), CH$_3$CH$_2$CH$_2$CO$_2$-); MS (ci) 368 (M+1).

d) 2-Amino-6-methoxy-9-(5-O-valeryl-β-D-arabinofuranosyl)-9H-purine $^1$H-NMR (200 MHz, DMSO-d$_6$): δ 7.83 (s, 1H, H$_8$), 6.45 (s, 2H, 2-NH$_2$), 6.15 (d, 1H, J=3.7 Hz, H$_{1'}$), 5.76 (d, 1H, J=4.2 Hz, 2'-OH), 5.65 (d, 1H, J=3.5 Hz, 3'OH), 4.28 (m, 2H, H$_{2'}$ and H$_{3'}$), 4.08 (m, 2H H$_{5'}$), 3.94 (s, 3H, —OCH$_3$) 3.92 (m, 1H, H$_{4'}$), 2.29 (t, 2H, J=7.1 Hz, CH$_3$CH$_2$CH$_2$C H$_2$CO$_2$-), 1.49 (m, 2H, CH$_3$CH$_2$CH$_2$CH$_2$CO$_2$-) 1.28 (m, 2H CH$_3$CH$_2$CH$_2$CH$_2$CO$_2$-), 0.83 (t, 3H, J=7.2 Hz, CH$_3$CH$_2$CH$_2$CH$_2$CO$_2$-).

e) 2-Amino-6-methoxy-9-(5-O-(4-methoxy-4-oxobutyryl)-β-D-arabinofuranosyl)-9H-purine (starting material trichloroethyl methyl succinate)

$^1$H-NMR 200 MHz, DMSO-d$_6$): δ 7.83 (s, 1H, H$_8$), 6.45 (s, 2H, 2-NH$_2$), 6.15 (d, 1H, J=3.7 Hz, H$_{1'}$), 5.75 (d, 1H, J=4.3 Hz, 2'-OH), 5.65 (d, 1H, J=3.7 Hz, 3'-OH), 4.28 (m, 2H, H$_{2'}$ and H$_{3'}$), 4.08 (m, 2H, H$_{5'}$), 3.95 (s, 3H, —OCH$_3$) 3.91 (m, 1H, H$_{4'}$), 3.51 (s, 3H, CH$_3$OC(O)-), 2.56 (s, 4H, —OC(O)CH$_2$CH$_2$C(O)O-); MS (CI) 412 (M+1), 280 (M—C$_5$H$_7$O$_4$). Anal. Calcd. for $C_{16}H_{21}N_5O_8$·0.40 $H_2O$: Calcd: C, 45.64; H, 5.28; N, 16.63. Found: C, 45.62; H, 5.21; N, 16.67.

EXAMPLE 2

Chemical Synthesis of Esters of the Present Invention a(i) 2-Amino-9-(2,5-di-O -tert-butyldimethylsilyl-β-D-arabinofuranosyl)-6-methoxy-9H-purine 2-Amino-9-(β-D-arabinofuranosyl)-6-methoxy-9H-purine (10 g, 34 mmol) was added to a 500 mL round bottom flask and dried by coevaporation with pyridine (2×50 mL). Imidazole (11 g, 160 mmol) was added, followed by tert-butyldimethylsilyl chloride (11 g, 74 mmol). The flask was flushed with argon and fitted with a septum. Dry dimethylformamide (DMF, 40 mL) was added and the solution was stirred at room temperature for 18 hours. TLC on silica gel with acetone:CHCl$_3$ (1:10) showed that about 20% of the staring material remained (R$_f$=0.05) and that three higher R$_f$ spots had formed at 0.18, 0.41 and 0.75. Additional tert-butyldimethylsilyl chloride (1.0 g, 6.6 mmol) was added and stirring was continued for 24 hours. TLC in the same solvent subsequently showed all the starting material was consumed.

The DMF was then removed under reduced pressure and the residue was partitioned between ethyl acetate (350 mL) and $H_2O$ (100 mL and 3×50 mL). The aqueous layers were back extracted with ethyl acetate (100 mL) and the combined organic layers were dried (MgSO$_4$), filtered, and concentrated. Crude product was purified on a silica gel flash column (5×25 cm) eluted with a step gradient of acetone in CHCl$_3$ (1:20 to 1:2). Three product fractions were obtained corresponding to the three spots observed by TLC. The R$_f$=0.18 fraction provided 4.0 g (23%) of a white solid identified as the 2,5-disilylated product: m.p.=180°-182° C. (uncorrected); UV $\lambda_{max}$ (95% EtOH): 248.8 nm and 280.8 nm; MS (EI): m/z 468 ($C_{19}H_{34}N_5O_5Si_2$), 450 ($C_{19}H_{32}N_5O_4Si_2$), 336 ($C_{13}H_{18}N_5O_4Si$) 322 ($C_{14}H_{24}N_5O_2Si$), 264 ($C_{10}H_{14}N_5O_2Si$) 222 ($C_8H_8N_5O_3$), 208 ($C_8H_{10}N_5O_2$), 194 ($C_7H_8N_5O_2$), 166 ($C_6H_8N_5O$), 133 ($C_6H_{17}OSi$), 115 ($C_6H_{15}Si$), 57 ($C_4H_9$). $^1$H-NMR (CDCl$_3$): δ 7.87 (s, 1H, H-8), 6.29 (d, 1H, H-1', J=4.6 Hz), 4.82 (br s, 2H NH$_2$), 4.39–4.34 (m, 2H, H-2' and 3'), 4.07 (s, 3H, —OCH$_3$), 3.94–3.82 (m, 3H, H-4' and 5'), 2.40 (br s, 1H, 3'-OH), 0.91 (s, 9H, (CH$_3$)$_3$CSi), 0.71 (s, 9H, (CH$_3$)$_3$CSi), 0.09 (s, 6H, (CH$_3$)$_2$Si), −0.02 (s, 3H, (CH$_3$)Si), −0.24 (s, 3H, (CH$_3$)Si). Anal. Calcd. for $C_{23}H_{43}N_5O_5Si_2$: Calcd: C, 52.54; H, 8.24; N, 13.32. Found: C, 52.28; H, 8.20; N, 13.17.

a(ii) 2-Amino-9-(2,5-di-O-tert-butyldimethylsilyl-3-O-pivaloyl -β-D-arabinofuranosyl)-6-methoxy-9H-purine 2-Amino-9-((2,5-di-O-tert-butyldimethylsilyl)-β-D-arabinofuranosyl)-6-methoxy-9H-purine (2.0 g, 3.8 mmol) was weighed into a flame dried 250 mL round bottom flask.

4-N,N-Dimethylaminopyridine (0.05 g, 0.4 mmol) was added and the flask was flushed with argon and sealed with a septum. Dry acetonitrile (50 mL), triethylamine (8.0 mL), and pivalic anhydride (3 mL, 14.8 mmol) were added to the reaction mixture. After 158 hours, the reaction mixture was concentrated and the residue was taken up in ethyl acetate (250 mL) and extracted with $H_2O$ (3×50 mL). The ethyl acetate was dried ($MgSO_4$), filtered, and concentrated to give 3.8 g of a yellow oil. A 300 mg portion of this material was purified on a Chromatotron (Harrison Scientific) fitted with a 4 mm silica gel rotor, eluting with acetone:$CHCl_3$ (1:10). The product was isolated as a clear gum (0.176 g); MS (EI): m/z 609 ($C_{28}H_{51}N_5O_6Si_2$), 594 ($C_{27}H_{48}N_5O_6Si_2$), 552 ($C_{24}H_{42}N_5O_6Si_2$), 450 ($C_{19}H_{32}N_5O_4Si_2$), 322 ($C_{14}H_{24}N_5O_2Si$), 314 ($C_{16}H_{30}O_4Si$), 194 ($C_7H_8N_5O_2$), 166 ($C_6H_8N_5O$), 57 ($C_4H_9$). $^1$H-NMR ($CDCl_3$): δ 7.93 (s, 1H, H-8), 6.25 (d, 1H, H-1', J=3.8 Hz), 5.28 (d, 1H, H-3', J=2.2 Hz), 5.05 (br 3, 2H, $NH_2$), 4.30 (dd, 1H, H-2', $J_{2',3}$=1.8 Hz), 4.10 (s, 3H, —$OCH_3$), 4.04 (dt, 1H, H-4', J=2.5 Hz, J=5.9 Hz), 3.19 (d, 2H, H-5', J=5.5 Hz, 1.27 (s, 9H, —OCOC($CH_3$)$_3$), 0.90 (s, 9H, —SiC($CH_3$)$_3$), 0.75 (s, 9H, —SiC($CH_3$)$_3$), 0.09 (s, 6H —Si($CH_3$)$_2$), 0.02 (s, 3H, —Si($CH_3$)), -0.33 (s, 3H, —Si($CH_3$)). Anal. Calcd. for $C_{28}H_{51}N_5O_6Si_2$·0.75 $C_3H_6O$·0.05$CHCl_3$: Calcd: C, 55.19; H, 8.49; N, 10.62 Found: C, 55.32; H, 8.61; N, 10.53 b) 2-Amino-6-methoxy-9-(3-O-pivaloyl-β-D-arabinofuranosyl)-9H-purine

2-Amino-6-methoxy-9-[(3-O-pivaloyl-2,5-di-O-tert-butyldimethylsilyl)-β-D-arabinofuranosyl)-]-9H-purine (2.1 g, 3.4 mmol) was taken up in THF (40 mL) and cooled in an ice bath to 5° C. $H_2O$ (2 mL) was added, followed by tetrabutylammonium fluoride (TBAF) as a 1M solution in THF (10 mL, 10 mmol). After 2 hours at 5° C., an additional 10 mL of TBAF was added. After two hours, the reaction was treated with yet an additional 5 mL of TBAF and allowed to stir for eighteen hours more. The reaction mixture was then diluted with $CHCl_3$ (40 mL) and passed through a pad of silica gel (230–400 mesh, 5×5 cm) with 1:1 acetone:$CHCl_3$ (500 mL). The filtrate was concentrated and added to a silica gel column (230–400 mesh, 5×18 cm). The column was eluted with a step gradient of acetone in $CHCl_3$ (1:10 to 1:1 acetone:$CHCl_3$). Two main fractions were obtained from the column corresponding to material with an $R_f$=0.74 and 0.50 in acetone:$CHCl_3$ (1:1). The lower $R_f$ material was isolated as a white powder 0.77 g (53%) and was shown to be the desired 3'-O-pivaloyl derivative: m.p. 241°–243° C. (uncorrected); UV $\lambda_{max}$ (ε): pH =7.00: 278.9 nm (8,700) and 247.7 nm (8,900); 0.1N HCl: 287.0 (8,600) and 243.7 (6,800); 0.1N NaOH: 279.2 (8,900) and 247.7 (8,200); MS (EI): m/z 381 (M, $C_{16}H_{23}N_5O_6$), 366 ($C_{15}H_{20}N_5O_6$), 296 ($C_{11}H_{14}N_5O_5$), 280 ($C_{11}H_{14}N_5O_4$), 250 ($C_{10}H_{12}N_5O_3$), 232 ($C_{10}H_{10}N_5O_2$), 208 ($C_8H_{10}N_5O_2$), 194 ($C_7H_8N_5O_2$), 165 ($C_6H_7N_5O$), 136 $C_5H4N4O$), 85 ($C_5H_9O$); IR (KBr): 1733.6, 1594.7 cm-1. $^1$H-NMR ($Me_2SO$-$d_6$): δ 7.95 (s, 1H, H-2), 6.45 (br s, 2H, $NH_2$), 6.10 (d, 1H, H-1', J=4.3 Hz), 6.10 (d, 1H, 2'-OH, J=5.5 Hz), 5.16–510 (m, 2H, H-3' and 5'-OH), 4.23–4.20 (m, 1H, H-2'), 3.94 (s, 3H, Pur-$OCH_3$), 3.90–3.86 (m, 1H, H-4'), 3.67–3.60 (m, 2H, 5'), 1.18 (s, 9H, C($CH_3$)$_3$). Anal. Calcd. for $C_{16}H_{23}N_5O_6$·0.40 $CHCl_3$: Calcd: C, 45.90; H, 5.50; N, 16.32. Found: C, 45.72; H, 5.43; N, 16.04.

c(i) 2-Amino-9-(3,5-di-O-tert-butyldimethylsilyl-β-D-arabinofuranosyl)-6-methoxy-9H-purine 2-Amino-9-(β-D-arabinofuranosyl)-6-methoxy-9H-purine (10 g, 34 mmol) was added to a 500 mL round bottom flask and dried by coevaporation with pyridine (2×50 mL). Imidazole (11 g, 160 mmol) was added, followed by tert-butyldimethylsilyl chloride (11 g, 74 mmol). The flask was flushed with argon and fitted with a septum. Dry dimethylformamide (DMF, 40 mL) was added and the solution was stirred at room temperature for 18 hours. TLC on silica gel with acetone:$CHCl_3$ (1:10) showed that about 20% of the staring material remained ($R_f$=0.05) and that three higher $R_f$ spots had formed at 0.18, 0.41 and 0.75. Additional tert-butyldimethylsilyl chloride (1.0 g, 6.6 mmol) was added and stirring was continued for 24 hours. TLC in the same solvent subsequently showed all the starting material was consumed.

The DMF was then removed under reduced pressure and the residue was partitioned between ethyl acetate (350 mL) and $H_2O$ (100 mL and 3×50 mL). The aqueous layers were back extracted with ethyl acetate (100 mL) and the combined organic layers were dried ($MgSO_4$), filtered, and concentrated. Crude product was purified on a silica gel flash column (5×25 cm) eluted with a step gradient of acetone in $CHCl_3$ (1:20 to 1:2). Three product fractions were obtained corresponding to the three spots observed by TLC. The $R_f$=0.41 fraction provided 8.0 g (45%) of a white solid identified as the 3,5-disilylated product: m.p.=88°–90° C. (uncorrected); UV $\lambda_{max}$ (95% EtOH): 247.1 nm and 280.1 nm; MS (EI): m/z 526 (M+H, $C_{23}H_{44}N_5O_5Si_2$), 510 ($C_{22}H_{40}N_5O_5Si_2$), 468 ($C_{19}H_{34}N_5O_5Si_2$), 336 ($C_{13}H_{18}N_5O_4Si$), 301 ($C_{13}H_{25}O_4Si_2$), 261 ($C_{11}H_{11}N_5O_3$), 231 ($C_{10}H_9N_5O_2$), 208 ($C_8H_{10}N_5O_2$), 194 ($C_7H_8N_5O_2$), 165 ($C_6H_7N_5O$), 133 ($C_6H_{17}OSi$), 115 ($C_6H_{15}Si$), 57 ($C_4H_9$). $^1$H-NMR ($CDCl_3$): δ 8.01 (s, 1H, H-8), 6.16 (d, 1H, H-1', J=3.1 Hz), 5.08 (br s, 1H, 2'-OH), 4.84 (br s, 2H, $NH_2$), 4.31 (t, 1H, H-3', J=1.8 Hz), 4.16–4.13 (m, 1H, H-2'), 4.05 (s, 3H, —$OCH_3$), 4.02–3.99 (m, 1H, H-4'), 3.94 (dd, 1H, H-5', $J_{4',5}$=3.7 Hz, $J_{5',5}$=11.0 Hz), 3.79 (dd, 1H, H-5", $J_{4',5}$=2.7 Hz, $J_{5',5"}$=11.0 Hz), 0.94 (s, 9H, ($CH_3$)$_3$CSi), 0.93 (s, 9H, ($CH_3$)$_3$CSi), 0.17 (s, 3H, $CH_3$Si), 0.14 (s, 3H, $CH_3$Si), 0.12 (s, 6H, ($CH_3$)$_2$Si). Anal. Calcd. for $C_{23}H_{43}N_5O_5Si_2$: Calcd: C, 52.54; H, 8.24; N, 13.32 Found: C, 52.32; H, 8.24; N, 13.25 c(ii) 2-Amino-9-(3,5-di-O-tert-butyldimethylsilyl-2-O-valeryl-β-D-arabinofuranosyl)-6-methoxy-9H-purine 2-Amino-9-[(3,5, -di-O-tert-butyldimethylsilyl)-β-D-arabinofuranosyl]-6-methoxy-9H-purine (1.3 g, 2.5 mmol) was weighed into a flame dried 250 mL round bottom flask. 4-N,N-Dimethylaminopyridine (0.05 g, 0.4 mmol) was added and the flask was flushed with argon and sealed with a septum. Dry acetonitrile (30 mL), triethylamine (5.0 mL) were added and the solution was cooled in an ice bath. Valeric anhydride (0.6 mL, 3.0 mmol) was added to the reaction mixture. After 18 hours at 0.5° C., the reaction mixture was concentrated and the residue was taken up in hexane:ethyl acetate (1:1) (200 mL) and extracted with $H_2O$ (3 ×50 mL). The organic layer was dried ($MgSO_4$) filtered, and concentrated to give 1.7 g of a yellow oil. A 270 mg portion of this material was purified on a Chromatotron (Harrison Scientific) fitted with a 2 mm silica gel rotor. The rotor was eluted with acetone:$CHCl_3$ (1:10). The product off the Chromatotron was a white solid (0.21 g, 0.34 mmol): m.p.=105°–107° C. (uncorrected); MS (EI): m/z 609 ($C_{28}H_{51}N_5O_6Si_2$), 594 ($C_{27}H_{48}N_5O_6Si2$), 552 ($C_{24}H_{42}N_5O_6Si_2$), 420 ($C_{18}H_{28}N_5O_5Si$), 292 ($C_{13}H_{18}N_5O_3$), 261 ($C_{12}H_{15}N_5O_2$), 231 ($C_{10}H_9N_5O_2$), 194 ($C_7H_8N_5O_2$), 166 ($C_6H_8N_5O$), 159 ($C_7H_{25}O_2Si$), 57 ($C_4H_9$). $^1$H-NMR ($CDCl_3$): δ 7.92 (s, 1H, H-8), 6.39 (d, 1H, H-1', J=5.7 Hz), 5.33 (t, 1H, H-2', J=5.7 Hz), 4.84 (br s, 2H, $NH_2$), 4.60 (t, 1H, H-3', J=5.7 Hz), 4.05 (s, 3H, $OCH_3$), 3.93–3.80 (m, 1H, H-4' and H-5'), 2.09 (dt, 1H, C(O)$CH_2$, J=7.5 Hz) 1.94 (dt, 1H, C(O)$CH_2$, J=7.5 Hz, J=15 Hz), 1.32–1.00 (m, 4H, —CH$_2$CH$_2$–), 0.93 (s, 9H, —SiC(CH$_3$)$_3$), 0.89 (s, 9H, —SiC(C$_3$)$_3$), 0.76 (t, 3H, —CH$_3$, J=7.0 Hz); 0.11 (s, 3H, Si(CH$_3$)), 0.09 (s, 3H, —Si(CH$_3$)), 0.09 (s, 3H, —Si(CH$_3$)), 0.08 (s, 3H, —Si(CH$_3$)). Anal. Calcd. for C$_{28}$H$_{51}$N$_5$O$_6$Si$_2$: Calcd: C, 55.14; H, 8.43; N, 11.48. Found: C, 55.09; H, 8.45; N, 11.46 c(iii) 2-Amino-6-methoxy-9-(2-O-valeryl-β-D-arabinofuranosyl)-9H-purine

2-Amino-9-(3,5-di-O-tert-butyldimethylsilyl-2-O-valeryl-β-D-arabinofuranosyl)-6-methoxy-9H-purine (1.4 g, 2.3 mmol) was taken up in tetrahydrofuran (THF, 40 mL) and cooled in an ice bath to 5° C. Acetic acid (0.06 mL, 10 mmol) was added, followed by tetrabutylammonium fluoride (TBAF) as a 1M solution in THF (10 mL, 10 mmol). After 18 hours at 5° C., the reaction mixture was diluted with CHCl$_3$ (40 mL) and passed through a pad of silica gel (230–400 mesh, 5×5 cm) with 1:1 acetone:CHCl$_3$ (500 mL). The filtrate was concentrated and purified on a Chromatotron fitted with a 4 mm rotor and eluted with neat ethyl acetate. Pure product was obtained from the column as a white foam 0.72 g (78%) after drying and was shown to be the desired 2'-O-valeryl derivative: m.p.: 83°–86° C. (uncorrected); UVλ$_{Max}$(ε): pH =7.00: 280.0 nm (7,800), 247.8 nm (8,400); 0.1N HCl: 278.6 (8,000), 247.7 (7,400); 0.1N NaOH: 286.2 (7,600), 244.9 (7,200); MS (EI): m/z 381 (C$_{16}$H$_{23}$N$_5$O$_6$), 351 (C$_{15}$H$_{21}$N$_5$O$_5$), 292 (C$_{13}$H$_{18}$N$_5$O$_3$), 279 (C$_{11}$H$_{13}$N$_5$O$_4$), 217 (C$_{10}$H$_{17}$O$_5$), 194 (C$_7$H$_8$N$_5$O$_2$), 165 (C$_6$H$_7$N$_5$O), 135 (C$_5$H$_5$N$_4$), 85 (C$_5$H$_9$O). IR (KBr) 1745.2, 1613.3 and 1588.7 cm$^{-1}$. $^1$-NMR (Me$_2$SO-d$_6$): δ 7.93 (s, 1H, H-2), 6.46 (br s, 2H, NHH2), 6.26 (d, 1H, H-1', J=5.9 Hz), 5.79 (d, 1H, 3'-OH, J=5.1 Hz), 5.23 (t, 1H, H-2', J=5.8 Hz), 5.02 (t, 1H, 5'-OH, J=5.6 Hz), 4.36 (ddd, 1H, H-3', J$_{3',3'-OH}$=5.1 Hz, J$_{2',3}$=5.7 Hz, J$_{3',4}$=5.8 Hz), 3.93 (s, 3H, Pur-OCH$_3$), 3.83–3.78 (m, 1H, H-4'), 3.68–3.61 (m, 2H, H-5'), 2.09 (dt, 1H, C(O)CH$_2$, J=7.5 Hz, J=15 Hz), 1.93 (dt, 1H, C(O)CH$_2$, J=7.5 Hz, J=15 Hz), 1.30–0.90 (m, 4H, —CH$_2$CH$_2$–), 0.65 (t, 3H, —CH$_3$, J=7 Hz). Anal. Calcd. for C$_{16}$H$_{23}$N$_5$O$_6$.0.15 C$_5$H$_{10}$O$_3$: Calcd: C, 50.41; H, 6.22; N, 17.29. Found: C, 50.41; H, 6.59; N, 17.40.

d(i) 2-Amino-9-(3-O-benzoyl-2,5-di-O-tert-butyldimethylsilyl-β-D-arabinofuranosyl)-6-methoxy-9H-purine 2-Amino-9-((2,5-di-O-tert-butyldimethylsilyl)-β-D-arabinofuranosyl]-6-methoxy-9H-purine (1.5 g, 2.9 mmol) was weighed into a flame dried 250 mL round bottom flask. 4-N,N-Dimethylaminopyridine (0.05 g, 0.4 mmol) was added and the flask was flushed with argon and sealed with a septum. Dry acetonitrile (50 mL), triethylamine (5.0 mL), and benzoic anhydride (0.77 g, 3.4 mmol) were added to the reaction mixture. After 5 hours at ambient temperature, the reaction mixture was concentrated and the residue was taken up in ethyl acetate (250 mL) and extracted with H$_2$O (2×50 mL). The ethyl acetate was dried (MgSO$_4$), filtered, and concentrated to give 3.8 g of a yellow oil. A 270 mg portion of this material was purified on a Chromatotron (Harrison Scientific) fitted with a 4 mm silica gel rotor. The rotor was eluted with acetone:CHCl$_3$ (1:10). The product off the Chromatotron was a white solid (0.18 g, 0.29 mmol): m.p.=73°–75° C. (uncorrected); MS (EI): m/z 630 (C$_{30}$H$_{48}$N$_5$O$_6$Si$_2$), 614 (C$_{29}$H$_{44}$N$_5$O$_6$Si$_2$), 572 (C$_{26}$H$_{44}$N$_5$O$_6$Si$_2$), 451 (C$_{19}$H$_{33}$H$_5$O$_4$Si$_2$), 194 (C$_7$H$_8$N$_5$O$_2$), 179 (C$_6$H$_5$N$_5$O$_2$), 166 (C$_6$H$_8$N$_5$O), 166 (C$_6$H$_8$N$_5$O), 105 (C$_7$H$_5$O). $^1$H-NMR (CDCl$_3$): δ 8.12–8.07 (m, 2H, Ar—H), 7.92 (s, 1H, H-8), 7.63–7.45 (m, 3H, Ar—H), 6.33 (d, 1H, H-1', J=3.7 Hz), 5.46 (t, 1H, H-3', J=1.8 Hz), 4.79 (br s, 2H, NH$_2$), 4.42 (dd, 1H, H-2', J$_{1,2}$=3.7 Hz and J$_{2',3}$=1.7 Hz), 4.30–4.20 (m, 1H, H-4'), 4.07 (s, 3H, —OCH$_3$), 3.99–3.95 (m, 2H, H-5'), 0.89 (s, 9H, —SiC(CH$_3$)$_3$), 0.76 (s, 9H, —Si(CH$_3$)$_3$), 0.09 (s, 6H, —Si(CH$_3$)$_2$), 0.03 (s, 3H, —Si(CH$_3$)), –0.34 (s, 3H, —Si(CH$_3$)): Anal. Calcd. for C$_{30}$H$_{47}$N$_5$O$_6$Si$_2$: Calcd: C, 57.20; H, 7.52; N, 11.12. Found: C, 57.08; H, 7.59; N, 11.05.

d(ii) 2-Amino-9-(3-O-benzoyl-β-D-arabinofuranosyl)-6-methoxy-9H-purine

2-Amino-9-(3-O-benzoyl-2,5-di-O-tert-butyldimethylsilyl)-β-D-arabinofuranosyl]-6-methoxy-9H-purine (1.97 g, 2.6 mmol) was taken up in tetrahydrofuran (THF, 40 mL) and cooled in an ice bath to 5° C. Acetic acid (0.6 mL, 10 mmol) was added, followed by tetrabutylammonium fluoride (TBAF) as a 1M solution in THF (10 mL, 10 mmol). After 18 hours at 5° C., the reaction mixture was diluted with CHCl$_3$ (40 ml) and passed through a pad of silica gel (230–400 mesh, 5×5 cm) with 1:1 acetone:CHCl$_3$ (500 mL). The filtrate was concentrated to a white solid which was adsorbed onto 10 g of silica gel and added to a silica gel column (230–400 mesh, 5×18 cm). The column was eluted with acetone:CHCl$_3$ (1:2). Pure product was obtained from the column corresponding to material with an R$_f$=0.56 in acetone:CHCl$_3$ (1:1). This material was a white powder 0.77 g (1.9 mol) after drying and was shown to be the desired 3'-O-benzoyl derivative: m.p. 155°–157° C. (uncorrected); UV λ$_{max}$ (ε): pH =7.00: 278.3 nm (10,100), 235.2 nm (18,800); 0.1N HCl: 278.1 (9,100), 245 (sh) (9,600); 0.1N NaOH: 284.8 (9,600), 233.9 (18,400); MS (EI): m/z 401 (M, C$_{18}$H$_{19}$N$_5$O$_6$), 296 (C$_{11}$H$_{14}$N$_5$O$_5$), 250 (C$_{10}$H$_{12}$N$_5$O$_3$), 232 (C$_{10}$H$_{10}$N$_5$O$_2$), 20 (C$_8$H$_{10}$N$_5$O$_2$), 194 (C$_7$H$_8$N$_5$O$_2$), 179 (C$_7$H$_7$N$_4$O$_2$), 165 (C$_6$H$_7$N$_5$O), 136 (C$_5$H$_4$N$_5$), 122 (C$_7$H$_5$O$_2$), 105 (C$_7$H$_5$O); IR (KBr): 1714.6, 1611.8 and 1591.7 cm$^{-1}$. $^1$H-NMR (Me$_2$SO-d$_6$): δ 8.06 (s, 1H, H-2), 8.02–8.00 (m, 2H, Ar—H), 7.71 (t, 1H, Ar—H, J=7.3 Hz), 7.57 (t, 2H, Ar—H, J=7.4 Hz), 6.45 (br s, 2H, NH$_2$), 6.20 (d, 1H, H-1', J=4.3 Hz), 6.12 (d, 1H, 2'-OH, J=5.5 Hz), 5.41 (t, 1H, H-3', J=2.9 Hz), 5.20 (t, 1H, 5'-OH, J=5.5 Hz), 4.43–4.37 (m, 1H, H-2'), 4.17–4.11 (m, 1H, H-4'), 3.95 (s, 3H, Pur-OCH$_3$), –0.79–3972 (m, 2H, 5'). Anal. Calcd. for C$_{18}$H$_{19}$N$_5$O$_6$.0.60 C$_3$H$_6$O.0.05 CHCl$_3$: Calcd: C, 53.92; H, 5.16; N, 15.84. Found: C, 53.81; H, 5.10; N, 15.76.

e(i) 2-Amino-9-(3,5-di-O-tert-butyldimethylsilyl-2-O-pivaloyl-β-D-arabinofuranosyl)-6-methoxy-9H-purine 2-Amino-9-(3,5-di-O-tert-butyldimethylsilyl-β-D-arabinofuranosyl)-6-methoxy-9H-purine (1.3 g, 2.5 mmol) was weighed into a flame dried 250 mL round bottom flask. 4-N,N-Dimethylaminopyridine (0.05 g, 0.4 mmol) was added and the flask was flushed with argon and sealed with a septum. Dry acetonitrile (30 mL), triethylamine (5.0 mL) and pivalic anhydride (0.6 mL, 3.0 mmol) were added to the reaction mixture which was stirred at room temperature. After 160 hours, the reaction mixture was concentrated, the residue taken up in ethyl acetate (250 mL) and extracted with H$_2$O (3×50 mL). The ethyl acetate was collected, dried (MgSO$_4$), filtered, and concentrated to give 2.0 g of a yellow oil. A 250 mg portion of this material was purified on a Chromatotron (Harrison Scientific) fitted with a 2 mm silica gel rotor, eluted with acetone:CHCl$_3$ (1:10). The product off the Chromatotron was a clear gum (0.176 g); MS (EI): m/z 609 (C$_{28}$H$_{51}$N$_5$O$_6$SI$_2$), 594 (C$_{27}$H$_{48}$N$_5$O$_6$Si$_2$), 552 (C$_{24}$H$_{42}$N$_5$O$_6$Si$_2$), 420 (C$_{18}$H$_{28}$N$_5$O$_5$Si), 292 (C$_{13}$H$_{18}$N$_5$O$_3$), 261 (C$_{12}$H$_{15}$N$_5$O$_2$), 231 (C$_{10}$H$_9$N$_5$O$_2$), 194 (C$_7$H$_8$N$_5$O$_2$), 166 (C$_6$H$_8$N$_5$O), 159 (C$_7$H$_{15}$O$_2$Si), 57 (C$_{49}$). $^1$H-NMR (CDCl$_3$): δ 7.88 (s, 1H, H-8), 6.40 (d, 1H, H-1', J=5.9 Hz), 5.30 (t, 1H, H-2', J=6.0 Hz), 4.85 (br s, 2H, NHH2Y), 4.65 (t, 1H, H-3', J=6.0 Hz), 4.04 (s, 3H, OCH$_3$), 3.95–3.85 (m, 1H, H-4' and H-5'), 0.92 (s, 9H, OCOC(CH$_3$)$_3$), 0.89 (s, 9H, SiC(CH$_3$)$_3$, 0.88 (s, 9H, SiC(CH$_3$)$_3$), 0.13 (s, 3H, SiCH$_3$), 0.11 (s, 3H, SiCH$_3$), 0.08 (s, 3H, SiCH₃), 0.07 (s, 3H, SiCH₃). Anal. Calcd. for C₂₈H₅₁N₅O₆Si₂: Calcd: C, 55.14; H, 8.43; N, 11.48. Found: C, 54.97; H, 8.42; N, 11.10.

e(ii) 2-Amino-6-methoxy-9-(2-O-pivaloyl-β-D-arabinofuranosyl)-9H-purine

2-Amino-6-methoxy-9-(3,5-di-O-tert-butyldimethylsilyl-2-O-pivaloyl-β-D-arabinofuranosyl)9H-purine (1.3 g, 2.0 mmol) was taken up in tetrahydrofuran (THF, 40 mL) and cooled in an ice bath to 5° C. Acetic acid (0.06 mL, 10 mmol) was added, followed by tetrabutylammonium fluoride as a 1M solution in THF (10 mL, 10 mmol). After 24 hours at 5° C., the reaction mixture was diluted with CHCl₃ (40 mL) and passed through a pad of silica gel (230–400 mesh, 5×5 cm) with 1:1 acetone:CHCl₃ (500 mL). The filtrate was concentrated and applied to a silica gel column (230–400 mesh, 5×18 cm), eluted with acetone:CHCl₃ (1:2, 1.5 L), followed by acetone:CHCl₃ (1:1, 1.5 L). Pure product was obtained from the column as a white powder 0.76 g (100%) after drying and was shown to be the desired 2'-O-pivaloyl derivative: m.p.: 83°–85° C. (uncorrected); UV λ$_{max}$ (ε): pH=7.00: 279.7 nm (8,100), 247.9 nm (8,800); 0.1N HCl: 286.6 (7,300), 244.7 (6,200); 0.1N NaOH: 279.7 (8,000), 248.8 (7,900); MS (EI): m/z 250 (C₁₀H₁₂N₅O₃), 232 (C₁₀H₁₀N₅O₂), 217 (C₁₀H₁₇N₅), 208 (C₈H₁₀N₅O₂), 194 (C₇H₈N₅O₂), 165 (C₆H₇N₅O), 135 (C₅H₄N₄O₄), 101 (C₅H₉O₂), 85 (C₅H₉O); IR (KBr): 1734.2, 1616.3 and 2589.4 cm⁻¹; ¹H-NMR (Me₂SO-d₆): δ 7.97 (s, 1H, H-2), 6.47 (br s, 2H, NH₂), 6.26 (d, 1H, H-1', J=5.9 Hz), 5.79 (d, 1H, 3'-OH, J=5.3 Hz), 5.23 (dd, 1H, H-2', J$_{1',2}$=5.9 Hz, J$_{2',3}$=5.2 Hz), 5.06 (5, 1H, 5'-OH, J=5.5 Hz), 4.37 (ddd, 1H, H-3', J$_{3',3'\text{-}OH}$=5.3 Hz, J$_{2',3}$=5.2 Hz, J$_{3',4}$=6.9 Hz), 3.92 (s, 3H, Pur-OCH₃), 3.84–3.79 (m, 1H, H-4'), 3.68–3.62 (m, 2H, H-5'). Anal. Calcd. for C₁₆H₂₃N₅O₆·0.40 CHCl₃: Calcd: C, 45.90; H, 5.50; N, 16.32 Found: C, 46.03; H, 5.69; N, 16.03.

f(i) 2-Amino-9-(2-O-benzoyl-3,5-di-O-tert-butyldimethylsilyl-β-D-arabinofuranosyl) 6-methoxy-9H-purine 2-Amino-9-[(3,5-di-O-tert-butyldimethylsilyl)-β-D-arabinofuranosyl]-6-methoxy-9H-purine (1.3 g, 2.5 mmol) was weighed into a flame dried 250 mL round bottom flask. 4-N,N-Dimethylaminopyridine (0.05 g, 0.4 mmol) and benzoic anhydride (0.67 g, 3.0 mmol) were added and the flask was flushed with argon and sealed with a septum. Dry acetonitrile (30 mL) and triethylamine (5.0 mL) were then added, and the mixture stirred at room temperature. After 18 hours, the reaction mixture was concentrated and the residue was taken up in ethyl acetate (250 mL) and extracted with H₂O (3×50 mL). The ethyl acetate was dried (MgSO₄), filtered, and concentrated to give 1.76 g of a yellow oil. A 250 mg portion of this material was purified on a Chromatotron (Harrison Scientific) fitted with a 2 mm silica gel rotor. The rotor was eluted with acetone:CHCl₃ (1:10). The product off the Chromatotron was a white solid (0.21 g): m.p.: 129°–131° C. (uncorrected); MS (EI): m/z 629 (C₃₀H₄₇N₅O₆Si₂), 572 (C₂₆H₄₇N₅O₆Si₂), 440 (C₂₀H₂₂N₅O₅Si), 312 (C₁₅H₁₄N₅O₃), 261 (C₁₁H₂₅O₃Si₂), 231 (C₉H₁₉O₃Si₂), 194 (C₇H₈N₅O₂), 166 C₆H₈N₅O), 105 (C₇H₅O). ¹H-NMR (CDCl₃): δ 8.07 (s, 1H, H-8), 7.67 (dd, 2H, Ar—H, J=1.0 Hz, J=8.2 Hz), 7.50 (tt, 1H, Ar—H, J=2.0 Hz, J=8.0 Hz), 7.30 (t, 2H, Ar—H, J=7.5 Hz), 6.48 (d, 1H, H-1', J=5.5 Hz), 5.63 (t, 1H, H-2', J=5.5 Hz), 4.74 (t, 1H, H-3', J=5.6 Hz), 4.68 (br. s, 2H, NH₂), 3.98 (s, 3H, —OCH₃), 4.00–3.80 (m, 3H, H-4' and H-5'), 0.92 (s, 9H, —SiC(CH₃)₃), 0.88 (s, 9H, —SiC(CH₃)₃), 0.12 (s, 3H, —Si(CH₃)), 0.09 (s, 3H, —Si(CH₃)), 0.08 (s, 3H, —Si(CH₃)), 0.06 (s, 3H, —Si(CH₃)). Anal. Calcd. for C₃₀H₄₇N₅O₆Si₂: Calcd: C, 57.20; H, 7.52; N, 11.12. Found: C, 57.42; H, 7.57; N, 11.12.

f(ii) 2-Amino-9-(2-O-benzoyl-β-D-arabinofuranosyl)-6-methoxy-9H-purine

2-Amino-9-[(2-O-benzoyl-3,5-di-O-tert-butyldimethylsilyl)-β-D-arabinofuranosyl]-6-methoxy-9H-purine (1.26 g, 2.0 mmol) was taken up in tetrahydrofuran (THF, 40 mL) and cooled in an ice bath to 5° C. Acetic acid (0.06 mL, 10 mmol) was added, followed by tetrabutylammonium fluoride (TBAF) as a 1M solution in THF (10 mL, 10 mmol). After 24 hours at 5° C., the reaction mixture was diluted with CHCl₃ (40 mL) and passed through a pad of silica gel (230–400 mesh, 5×5 cm) with 1:1 acetone:CHCl₃ (500 mL). The filtrate was concentrated and applied to a silica gel column (230–400 mesh, 5×18 cm). The column was eluted with acetone:CHCl₃ (1:2, 1 L) followed by acetone:CHCl₃ (1:1, 1.5 L). Pure product was obtained from the column corresponding to material with an R$_f$=0.33 in acetone:CHl₃ (1:1). This material was a white powder 0.74 g (90%) after drying and was shown to be the desired 2'-O-benzoyl derivative: m.p.: 82°–84° C. (uncorrected); UV λ$_{max}$ (ε): pH=7.00: 279.1 nm (8,600), 237.5 nm (17, 800); 0.1 N HCl: 277.8 (10,000), 245 (sh) (10,800); 0.1N NaOH: 286.1 (7,600), 236.4 (17,000). MS (EI): m/z 401 (M, C₁₈H₁₉N₅O₆), 371 (C₁₇H₁₇N₅O₅), 3.12 (C₁₅H₁₄N₅O₃), 279 (C₁₁H₁₃N₅₄), 237 (C₁₂H₁₃ O₅), 220 (C₁₂H₁₂N₄), 208 (C₈H₁₀N₅O₂), 194 (C₇H₈N₅O₂), 165 (C₆H₇N₅O), 135 (C₅H₅N₅), 105 (C₇H₅O); IR (KBr): 1725.3, 1613.6 and 1588.9 cm⁻¹; ¹H-NMR (Me₂SO-d₆): δ 8.04 (s, 1H, H-2), 7.70–7.57 (m, 3H, Ar—H), 7.47–7.39 (m, 2H, Ar—H), 6.44 (br. s, 2H, NH₂), 6.39 (d, 1H, H-1', J=5.6 Hz), 5.90 (d, 1H, 3'-OH, J=4.9 Hz), 5.48 (t, 1H, H-2', J=5.3 Hz), 5.07 (t, 1H, 5'-OH, J=5.6 Hz), 4.51 (apparent quartet, 1H, H-3', J$_{3',3}$'-OH –4.9 Hz, J$_{2',3}$=5.6 Hz, J$_{3',4}$=5.1 Hz), 3.87 (s, 3H, Pur-OCH₃), 3.94–3.83 (m, 1H, H-4'), 3.77–3.66 (m, 2H, H-5'). Anal. Calcd. for C₁₈H₁₉N₅O₆·0.20 C₃H₆O·0.50 CHCl₃: Calcd: C, 48.53; H, 4.41; N, 14.82 Found: C, 48.68; H, 4.54; N, 14.96 g(i) 2-Amino-9-(5-O-tert-butyldimethylsilyl-β-D-arabinofuranosyl)-6-methoxy-9H-purine 9-(β-D-arabinofuranosyl)-2-amino-6-methoxy-9H-purine (2.0 g, 6.7 mmol) was added to a 500 ml round bottom flask and dried by co-evaporation with pyridine (2×50 ml). Tert-butyldimethylsilyl chloride (1.2 g, 8 mmol) was added and the flask was flushed with argon and fitted with a septum. Dry acetonitrile (20 ml) and dry pyridine (20 ml) were added via syringe and needle. The solution was stirred at room temperature for 24 hours. TLC on silica gel with methanol : CHCl₃ (1:10) showed that all the starting material (R$_f$= 0.05) was used up and that one higher R$_f$ spot had formed (R$_f$=0.31). The reaction was treated with ethanol (2 ml) and concentrated under reduced pressure. The yellow residue was purified on a silica gel column (230–400 mesh, 5×18 cm) with methanol : CHCl₃ (1:20) as the eluting solvent. The column provided 1.6 g (3.9 mol) of a white solid after drying: m.p.=101°–103° C. (uncorrected): MS(EI): m/z 412 (M+H, C₁₇H₃₀N₅O₅Si), 396 (C₁₆H₂₆N₅O₅Si) 354 (C₁₃H₂₀N₅O₅Si), 208 (C₈H₁₀N₅O₂), 194 (C₇H₈N₅O₂), 178 (C₇H₈N₅O), 166 (C₆H₈N₅O), 165 (C₆H₇N₅O), 135 (C₅H₅N₅), 57 (C₄Hg); ¹H-NMR (Me₂SO-d₆, 300 MHz) 7.88 (s,1H, H-8), 6.49(br.s,2H,NH₂), 6.14 (d,1H, H-1',J=4.7 Hz), 5.67 (d,1H,2'- or 3'OH,J=5.0 Hz), 5.57 (d,1H,2'- or 3'OH, J=4.4 Hz), 4.15–4.09 (m,2H, H-2' and 3'), 3.98(s,3H,—OCH₃), 3.87–3.76 (m,3H, H-4' and 5'), 0.90 (s,9H,(CH₃)₃CSi), 0.07 (s,6H,(CH₃)₂Si); Anal.Calcd. for C₁₇H₂₉N₅O₅Si: Calcd: C, 49.62; H, 7.10; N, 17.02 Found: C, 49.36; H, 7.06; N, 16.88 g(ii) 9-(2,3-di-O-Acetyl-5-O-tert-butyldimethylsilyl-β-D-arabinofuranosyl)-2-amino-6-methoxy-9H-purine 2-Amino-9-(5-O-tert-butyldimethylsilyl-β-D-arabinofuranosyl)-6-methoxy-9H-purine (1.5 g, 3.5 mmol)

was weighed into a flame dried 100 mL round bottom flask fitted with a stir bar. Anhydrous acetonitrile (25 mL) was added followed by triethylamine (5 mL). 4-N,N-Dimethylaminopyrine (0.05 g, 0.4 mmol) was added and the flask was flushed with argon and sealed with a septum. Acetic anhydride (0.8 mL, 8.5 mmol, distilled neat) was added to the reaction mixture via syringe and needle. The reaction was stirred at ambient temperature (20° C.) and monitored by TLC on silica gel with 1:20 methanol: $CHCl_3$. After 18 hours all the starting material ($R_f$=0.34) was used up and one large product spot ($R_f$=0.77) had formed.

The reaction mixture was concentrated and the residue was taken up in ethyl acetate (250 mL) and extracted with $H_2O$ (3×50 mL). The organic layer was dried with $MgSO_4$ (anhydrous), filtered and concentrated to give 1.7 g of a yellow oil. A 210 mg portion of this material was purified on a Chromatotron (Harrison Scientific) fitted with a 2 mm silica gel rotor. The rotor was eluted with acetone: $CHCl_3$ (1:10). Pure product was obtained as a white solid (0.16 g, 0.33 mmol) after drying: m.p.=58°–60° C. (uncorrected); MS (EI): m/z 497 ($C_{21}H_{35}N_5O_7Si$), 438 ($C_{17}H_{24}N_5O_7Si$), 396 ($C_{15}H_{22}N_5O_6Si$), 378 ($C_{15}H_{20}N_5O_5Si$), 336 ($C_{13}H_{18}N_5O_4Si$), 318 ($C_{13}H_{16}N_5O_3Si$), 273 ($C_{11}H_{18}O_6Si$), 250 ($C_{10}H_{12}N_5O_3$), 208 ($C_8H_{10}N_5O_2$), 194 ($C_7H_8N_5O_2$), 165 ($C_6H_7N_5O$), 135 ($C_5H_5N_5$). $^1$H-NMR($CDCl_3$, 200 MHz) δ 7.89 (s, 1H, H-8), 6.38 (d, 1H, H-1' J=4.6 Hz), 5.53–4.49 (m, 2H, H-2' and 3'), 4.85 (br. s, 2H, $NH_2$), 4.05 (s, 3H, —$OCH_3$), 4.04–4.00 (m, 1H, H-4'), 3.94–3.91 (m, 2H, H-5'), 2.12 (s, 3H, C(O)$CH_3$), 1.85 (s, 3H, C(O)$CH_3$), 0.92 (s, 9H, 31C($CH_3$)$_3$), 0.10 (s, 6H, Si($CH_3$)$_2$). Anal. Calcd. for $C_{21}H_{33}N_5O_7Si$ Calcd: C, 50.89; H, 6.71; N, 14.13 Found: C, 50.70; H, 6.75; N, 13.91.

g(iii) 9-(2,3-di-O-Acetyl-β-D-arabinofuranosyl)-2-amino-6-methoxy-9H-purine

The silylated intermediate 9(2,3-di-O-acetyl-5-O-tertbutyldimethylsilyl-β-D-arabinofuranosyl)-2-amino-6-methoxy-9H-purine (1.4 g, 2.9 mmol) was taken up in THF (40 mL) and cooled in an ice bath to 5° C. Acetic acid (0.25 mL, 16 mmol) was added, followed by tetrabutylammonium fluoride as a 1M solution in THF (9 mL, 9 mmol). After 28 hours at 5° C., TLC in acetone: $CHCl_3$ (1:1) showed that the starting material was used up ($R_f$=0.77) and one main lower $R_f$ spots had formed ($R_f$=0.32). TLC in methanol: $CHCl_3$ (1:10) showed one spot at $R_f$=0.41.

The reaction mixture was passed through a pad of silica gel (230–400 mesh, 3×5 cm) with 1:1 acetone: $CHCl_3$ (500 mL). The filtrate was concentrated and purified on a Chromatotron fitted with a 4 mm rotor and eluted with acetone: $CHCl_3$ (1:1). The product was obtained (0.95 g) was contaminated with tetrabutylammonium hydroxide. The product was purified on a 4 mm Chromatotron rotor with the same solvent which provided pure product 0.877 g (2.3 mmol):

M.p.: 100°–102° C. (uncorrected); UVλ$_{max}$(ε): pH=7.00: 279.0 nm (8,200), 247.3 nm (9,800); 0.1N HCl: 286.7 (8,500), 242.5 (6,100); 0.1N NaOH: 279.3 (8,200), 248.9 (7,700); MS (EI): m/z 381 ($C_{15}H_{19}N_5O_7$), 322 ($C_{13}H_{14}N_5O_5$), 292 ($C_{12}H_{12}N_5O_4$), 194 ($C_7H_8N_5O_2$), 165 ($C_6H_7N_5O$), 135 ($C_5H_5N_5$), 43 ($C_2H_3O$); $^1$H-NMR ($Me_2SO$-$d_6$, 200 MHz): δ 8.00 (s, 1H, H-8), 6.52 (br, s, 2H, $NH_2$), 6.30 (d, 1H, H-1', J=4.6 Hz), 5.43–5.35 (m, 2H, H-2' and 3'), 5.11 (t, 1H, 5'-OH, J=5.8 Hz), 4.04 (dd, 1H, H-4', J=4.5 Hz, J=8.6 Hz), 3.94 (s, 3H, Pur-$OCH_3$), 3.71–3.62 (m, 2H, H-5'), 2.09 (s, 3H, C(O)$CH_3$), 1.80 (s, 3H, C(O)$CH_3$); IR (KBr) 1748.4, 1613.1 and 1588.5 cm$^{-1}$;

Analysis calculated for $C_{15}H_{19}N_5O_7$·0.40 $CHCl_3$: C, 43.11; H, 4.56; N, 16.32. Found: C, 43.16; H, 4.69; N, 16.21.

h(i) 2-Amino-9-(2,3,5-tri-O-tert-butyldimethylsilyl-β-D-arabinofuranosyl)-6-methoxy-9H-purine 2-Amino-9-(β6-D-arabinofuranosyl)-6-methoxy-9H-purine (10 g, 34 mmol) was added to a 500 ml round bottom flask and dried by co-evaporation with pyridine (2×50 ml). Imidazole (11 g, 160 mmol) was added followed by tertbutyldimethylsilyl chloride (11 g, 74 mmol). The flask was flushed with argon and fitted with a septum. Dry dimethylformamide (DMF) (40 ml) was added via syringe and needle. The solution was stirred at room temperature for 18 hours. TLC on silica gel with acetone: $CHCl_3$ (1:10) showed that about 20% of the starting material remained ($R_f$=0.05) and that three higher $R_f$ spots had formed at 0.18, 0.41 and 0.75. Thus additional tertbutyldimethylsilyl chloride (1.0 g, 6.6 mmol) was added and stirring was continued for 24 hours. TLC in the same solvent subsequently showed all the starting material was used up. The DMF was then removed under reduced pressure and the residue was partitioned between ethyl acetate (350 ml) and $H_2O$ (100 ml and 3×50 ml). The aqueous layers were back extracted with ethyl acetate (100 ml) and the combined organics were dried ($MgSO_4$), filtered, and concentrated. Crude product was purified on a silica gel flash column (5×25 cm) eluted with a stepwise gradient of acetone in $CHCl_3$ from 1:20 to 1:2. Three product fractions were obtained corresponding to the three spots observed by TLC. The $R_f$=0.75 fraction provided 4.0 g (6.2 mmol, 19%) of a white solid identified as the trisilylated product: m.p.=63°–65° C. (uncorrected): UV λ$_{max}$ (95% ethanol): 249.2 nm and 281.3 nm: MS (EI): m/z 640 (M,$C_{29}H_{57}N_5O_5Si_3$), 582 ($C_{25}H_{48}N_5O_5Si_3$), 450 ($C_{19}H_{32}N_4O_4Si_2$), 322 ($C_{14}H_{24}N_5O_2Si$), 222 ($C_8H_8N_5O_3$), 194 ($C_7H_8N_5O_2$), 166 ($_6H_8N_5O$), 133 ($C_6H_{17}OSi$), 115 ($C_6H_{15}Si$), 57 ($C_4Hg$); $^1$H-NMR($CDCl_3$, 200 MHz) 7.82 (s,1H, H-8), 6.30 (d,1H, H-1', J=3.5 Hz), 4.82 (br.s,2H, $NH_2$), 4.31 (m.1H, H-3'), 4.10 (dd,1H, H-2', $J_{1',2}$=3.5 Hz and $J_{2',3}$=1.7 Hz), 4.06 (s,3H, —$OCH_3$), 4.00–3.90 (m, 1H, H-4'), 3.84–3.80 (m,2H, H-5'), 0.93 (s,9H,($CH_3$)$_3$CSi), 0.90 (s,9H,($CH_3$)$_3$CSi), 0.75 (s,9H, ($CH_3$)$_3$CSi), 0.14 (s,6H, ($CH_3$)$_2$Si), 0.07 (s,3H,($CH_3$)Si), 0.06 (s,3H, ($CH_3$)Si), —0.09 (s,3H,($CH_3$)Si), —0.38 (s,3H,($CH_3$)Si); Anal. Calcd. for $C_{29}H_{57}N_5O_5Si_3$: Calcd: C,54.42; H,8.98; N, 10.94 Found: C,54.36; H, 8.86; N, 10.87 h(ii) 2-Amino-9-(2,3-di-O-tert-butyldimethylsilyl-β-D-arabinofuranosyl)-6-methoxy-9H-purine 2-Amino-9-(2,3,5-tri-O-tertbutyldimethylsilyl-β-D-arabinofuranosyl)-6-methoxy-9-H-purine (2.0 g, 3.1 mmol) was added to a 250 ml round bottom flask and treated with 80% aqueous acetic acid.

The solution was heated at 50° C. for 20 hours. TLC in acetone: $CHCl_3$ (1:10) showed all the starting material was used up ($R_f$=0.59) and only product remained ($R_f$=0.19). The reaction mixture was concentrated on the rotoevaporator with several additions of $H_2O$ (5 ml) to remove the last traces of acetic acid, and placed on the vacuum pump for two hours. The residue was purified on a silica gel column (5×18 cm, 230–400 mesh) with methanol: $CHCl_3$ (1:30) as the eluting solvent. The product containing fractions provided 1.2 g (2.3 mmol) of a white solid identified as the 2,3-dislylated derivative: m.p.–93°–95° C. (uncorrected); MS(EI): m/z 526 ($C_{23}H_{44}N_5O_5Si_2$), 510 ($C_{22}H_{40}N_5O_5Si_2$), 468 ($C_{19}H_{34}N_5O_5Si_2$), 322($C_{14}H_{23}N_5O_2Si$), 306 ($C_{13}H_{20}N_5O_2Si$), 264 ($C_{10}H_{14}N_5O_2Si$), 208 ($C_8H_{10}N_5O_2$), 194 ($C_7H_8N_5O_2$), 166 ($C_6H_8N_5O$), 115 ($C_6H_{15}Si$), 57 ($C_4Hg$); $^1$H-NMR ($CDCl_3$, 200 MHz) 7.82 (s,1H, H-8), 6.45 (br.s.2H,$NH_2$), 6.14 (d,1H, H-1', J=4.1 Hz), 4.99 (t,1H,5'-OH, J=4.0 Hz), 4.29 (t,1H, H-3', J=2.9 Hz), 4.22(t,1H, H-2', J=4.5 Hz), 3.93 (s,3H, —$OCH_3$), 3.82–3.76 (m,1H, H-4'), 3.62–3.58 (m,2H, H-5'), 0.89 (s,9H,($CH_3$)$_3$CSi), 0.64 (s,9H, ($CH_3$)$_3$CSi), 0.13 (s,6H,($CH_3$)$_2$Si), —0.06 (s,3H,($CH_3$)Si), −0.39 (s,3H,(CH₃)Si); Anal. Calcd. for C₂₃H₄₃N₅O₅Si₂: Calcd: C, 52.54; H,8.24; N, 13.32 Found: C, 52.37; H,8.29; N,13.22 h(iii) 2-Amino-9-(2,3,-di-O-tert-butyldimethylsilyl-5-O-isobutyryl-β-D-arabinofuranosyl)-6methoxy-9H-purine 2-Amino-9-(2,3-di-O-tert-butyldimethylsilyl-β-D-arabinofuranosyl)-6-methoxy-9H-purine (1.3 g, 2.5 mmol) was weighed into a flame dried 250 mL round bottom flask. 4-N,N-Dimethylaminopyriine (0.05 g, 0.4 mmol) was added and the flask was flushed with argon and sealed with a septum. Dry acetonitrile (25 ml) and triethylamine (5 mL) were added. The flask was cooled in an ice bath and isobutyric anhydride (0.5 mL, 3.0 mol) was added to the reaction mixture. The reaction was allowed to slowly warm to ambient temperature (20° C.). After 22 hours the reaction was monitored by TLC on silica gel with methanol: CHCl₃ (1:20). No starting material (R_f=0.27) remained and one large product spot (R_f=0.63) had formed.

The reaction mixture was concentrated and the residue was taken up in ethyl acetate (250 mL) and extracted with H₂O (3×50 mL). The ethyl acetate layer was dried with MgSO₄ (anhydrous), filtered and concentrated to give 1.5 g of a yellow oil. A 200 mg portion of this material was purified on a Chromatotron (Harrison Scientific) fitted with a 2 mm silica gel rotor. The rotor was eluted with acetone: CHCl₃ (1:10), providing 0.16 g (0.27 mmol) of a white solid after drying. M.p.=56°–58° C. (uncorrected); MS (EI): m/z 596 (C₂₇H₄₉N₅O₆Si₂), 538 C₂₃H₄₀N₅O₆Si₂), 322 (C₁₄H₂₄N₅O₂Si), 318 (C₁₃H₂₄O₅Si₂), 264 (C₁₀H₁₆N₅O₂Si), 194 (C₇H₈N₅O₂), 166 (C₆H₈N₅O), 115 (C₆H₁₅Si). ¹H-NMR (CDCl₃, 200 MHz) δ 7.84 (s, 1H, H-8), 6.34 (d, 1H, H-1', J=3.3 Hz), 4.87 (br, s, 2H, NH₂), 4.39–4.27 (m, 2H, H-2' and 3'), 4.20–4.10 (m, 3H, H-4' and 5'), 4.06 (s, 3H, —OCH₃), 2.58 (septet, 1H, —OC(O)CH(CH₃)₂, J=7.0 Hz), 1.17 (dd, 6H, —OC(O)CH(CH₃)₂, J=7.0 Hz, J=1.9 Hz), 0.94 (s, 9H, —SiC(CH₃)₃), 0.77 (s, 9H, —SiC(CH₃)₃), 0.15 (s, 3H, —Si(CH₃)), 0.13 (s, 3H, —Si(CH₃)), 0.09 (s, 3H, —Si(CH₃)), 0.39 (s, 3H, —Si(CH₃)). Anal. Calcd. for C₂₇H₄₉N₅O₆Si₂.0.05 C₃H₆O.0.10CHCl₃: Calcd: C, 53.59; H, 8.15; N, 11.47 Found: C, 53.58; H, 8.23; N, 11.40 h(iv) 2-Amino-9-(5-O-isobutyryl-β-D-arabinofuranosyl)-6-methoxy-9H-purine

The silylated intermediate 2-amino-9-(2,3-di-O-tertbutyldimethyl silyl-5-O-isobutyryl-β-D-arabinofuranosyl)-6-methoxy-9H-purine (1.2 g 2.1 mmol) was taken up in THF (40 mL) and colled in an ice bath to 5° C. Acetic acid (0.25 mL, 16 mmol) was added, followed by tetrabutylammonium fluoride as a 1M solution in THF (6 mL, 6 mmol). After 70 hours at 0°–5° C., TLC in acetone: CHCl₃ (1:1) showed that no starting material remained (R_f=0.91) and one new lower R_f spot had formed (R_f=0.17).

The reaction mixture was passed through a pad of silica gel (230–400 mesh, 2×8 cm) with 1:1 acetone: CH₂Cl₂ (1.1 L). The filtrate was concentrated to a light gold residue. This residue was purified on the Chromatotron fitted with a 4 mm rotor with acetone: CH₂Cl₂ (1:1) as the eluting solvent. A white solid was obtained (0.67 g) which was contaminated with tetrabutylammonium hydroxide by ¹H-NMR. Repurification with the same solvent system provided product (0.57 g) which still contained a small amount of tetrabutylammonium hydroxide. A final repurification on a 4 mm Chromatotron rotor with neat ethyl acetate provided 0.44 g (1.2 mmol) of pure product after drying:

M.p.: 113°–115° C. (uncorrected); UVλ_max(ε): pH=7.00: 278.9 nm (7,800) and 247.6 nm (8,300); 0.1N HCl: 287.5 (7,000) and 242.8 (5,700); 0.1N NaOH: 279.0 (7,600) and 248.5 (7,100); MS (EI): m/z 208 (C₈H₁₀N₅O₂), 194 (C₇H₈N₅O₂), 178 (C₇H₈N₅O), 165 (C₆H₇N₅O), 135 (C₅H₅N⁵), 71 (C₄H₇O); ¹H-NMR (300 MHz, Me₂SO-d₆): δ 7.84 (s, 1H, H-8), 6.48 (br, s, 2H, NH₂), 6.16 (d, 1H, H-1', J=4.0 Hz), 5.77 (d, 1H, 2' or 3'-OH, J=4.6 Hz), 5.68 (d, 1H, 2' or 3'-OH, J=3.9 Hz), 4.35–4.23 (m, 2H, H-2' and 3'), 4.11–4.09 (m, 2H, H-5'), 3.96 (s, 3H, Pur—OCH₃), 3.95–3.92 (m, 1H, H-4'), 2.55 septet, 1H, —C(O)C H(CH₃)₂, J=7.0 Hz), 0.08 (dd, 6H, —C(O)CH(CH₃)₂, J=7.0 Hz, J=1.8 Hz); IR (KBr) 1734.3, 1616.0, 1592.5 cm⁻¹; Analysis calculated for C₁₅H₂₁N₅O₆.0.20 C₄H₈O₂: C, 49.29; H, 5.92; N, 18.19 Found: C, 49.09; H, 5.97; N, 18.16 i) 9-(2,3,5-tri-O-Acetyl-β-D-arabinofuranosyl)-2-amino-6-methoxy-9H-purine

2-Amino-9-(β-D-arabinofuranosyl)-6-methoxy-9 H-purine (2.5 g, 8.4 mmol) was added to a 250 mL round bottom flask and dried by co-evaporation with pyridine (2×25 mL). The residue was dried on the vacuum pump for two hours. 4-N,N-dimethylaminopyridine (0.10 g, 0.8 mmol) was added and the flask was flushed with argon and fitted with a septum. Dry acetonitrile (50 mL) was added followed by triethylamine (8.5 mL) and acetic anhydride (2.6 mL, 27.7 mmol). The solution was stirred at room temperature for 3 hours. TLC on silica gel with acetone: CHCl₃ (1:10) showed that all the starting material (R_f=0.05) was reacted and that one higher R_f spot had formed at R_f=0.18.

The reaction was quenched with ethanol (2 mL) and concentrated to dryness. The residue was partitioned between ethyl acetate (300 mL) and 5% NaCO₃ (50 mL). The organic layer was washed with H₂O (2×50 mL) and the combined aqueous layers were back extracted with ethyl acetate (100 mL). Finally, the combined organic extracts were dried (MgSO₄), filtered, and concentrated. Crude product was purified on a silica gel column (5×18 cm) eluted with acetone: CHCl₃ from 1:1. Product was obtained as a white solid, 3.38 g (7.98 mmol) after drying. This material was recrystallized from ethyl acetate and heptane to give 2.97 g (7.0 mmol) after drying:

M.P.=178°–180° C. (uncorrected): UVλ_max(ε): pH=7.00: 279.5 nm (8,500), 247.6 nm (9,100); 0.1N HCl: 287.2 (7,600), 244.4 (6,700); 0.1N NaOH: 278.9 (8,900), 249.0 (8,300); MS(EI): m/z 424 (M+H, C₁₇H₂₂N₅O₈), 380 (C₁₅H₁₈N₅O₇), 364 (C₁₅H₁₈N₅O₅), 259 (C₁₁H₁₅O₇), 194 (C₇H₈N₅O₂), 166 (C₆H₈N₅O), 165 (C₅H₇N₅O), 149 (C₅H₃N₅O), 139 (C₇H₇O₃), 42 (C₂H₂O); ¹H-NMR (Me₂SO-d₆, 200 MHz): δ 7.92 (s, 1H, H-8), 6.54 (br, s, 2H, NH₂), 6.35 (d, 1H, H-1', J=4.6 Hz), 5.46–5.40 (m, 2H, H-2' and 3'), 4.41–4.20 (m, 3H, H-4' and 5'), 3.94 (s, 3H, Pur—OOH₃), 2.10 (s, 3H, C(O)CH₃), 2.03 (s, 3H, C(O)CH₃), 1.80 (s, 3H, C(O)CH₃); Anaylsis calculated for C₁₇H₂₁N₅O₈: C, 48.23; H, 5.00; N, 16.54 Found: C, 48.32; H, 4.93; N, 16.24 j) 9-(3,5-di-O-Acetyl-β-D-arabinofuranosyl)-2-amino-6-methoxy-9H-purine

2-Amino-9-(2,3,5-tri-O-acetyl)-β-D-arabinofuranosyl)-6-methoxy-9-H-purine (2.0 g, 4.72 mmol) was added to a 250 ml round bottom flask along with sodium acetate (1.2 g, 14.2 mmol) and hydroxylamine hydrochloride (0.98 g, 14.2 mmol). The flask was flushed with argon and fitted with a stir bar and septum. Dry pyridine (25 ml) was added and the solution was stirred at room temperature for 7 hours. TLC on silica gel with acetone: CHCl₃ (1:10) showed that starting material (R_f=0.68) was reacted and that one lower spot had formed at R_f=0.47. The reaction was treated with acetone (20 ml) concentrated to dryness, taken up in acetone again (100 ml) and concentrated. The residue was taken up in acetone (100 ml) and filtered. The precipitate was washed with acetone and the filtrate was concentrated to a yellow oil. Crude product was purified on a silica gel column (5×18 cm) eluted with acetone: $CH_2Cl_2$ (1:1). Product was obtained as a white solid, 1.46 g (3.83 mmol) after drying. $^1H$ NMR showed that this material was a mixture of the 3,5 diacetate and the 2,5 diacetate. These two products were separated by recrystallization from dichloromethane and heptane with the 2,5-diacetate prcipitating first. The 3,5 diacetate was obtained as white crystals 0.796 g (2.08 mmol) after two recrystallizations: m.p.=109°–110° C. (uncorrected): $UV\lambda_{max}(\epsilon)$: pH=7.00: 278.9 nm (8,400), 247.9 nm (9,000); 0.1N HCl: 286.9 (8,300), 244.5 (7,300); 0.1N NaOH: 279.0 (8,500), 247.6(8,000); MS(EI):m/z 381 (M+H, $C_{15}H_{19}N_5O_7$), 338 ($C_{13}H_{16}N_5O_6$), 194 ($C_7H_8N_5O_2$), 166 ($C_6H_8N_5O$), 165 ($C_6H_7N_5O$), 135 $C_5H_5N_5$), 43 ($C_2H_3O$); $^1$N-NMR(Me$_2$SO-d$_6$, 200 MHz); δ 7.89 (s,1H, H-8), 6.50 (br.s.2H,NH$_2$, 6.18(d, 1H, H-1', J=4.9 Hz), 6.14 (d,1H,2'-OH, J=4.1 Hz), 5.10 (t, 1H, H-3', J=2.7 Hz), 4.42–4.23 (m, 3H, H-2' and 5'), 4.16–4.08 (m, 1H, H-4'), 3.95 (s,3H,Pur—OCH$_3$), 2.10 (s,3H,C(O)CH$_3$), 2.01 (s, 3H, C(O)CH$_3$); Anal. Calcd. for $C_{15}H_{19}N_5O_7 \cdot 0.10CH_2Cl_2$: Calcd: C,46.52; H,4.96; N,17.96 Found: C,46.31; H,5.13; N,17.70 k) 9-(2,5-di-O-Acetyl-β-D-arabinofuranosyl)-2-amino-6-methoxy-9H-purine

2-Amino-9-(2,3,5-tri-O-acetyl)-β-D-arabinofuranosyl)-6-methoxy-9-H-purine (2.0 g, 4.72 mmol) was added to a 250 ml round bottom flask along with sodium acetate (1.2 g, 14.2 mmol) and hydroxylamine hydrochloride (0.98 g, 14.2 mmol). The flask was flushed with argon and fitted with a stir bar and septum. Dry pyridine (25 ml) was added and the solution was stirred at room temperature for 7 hours. TLC on silica gel with acetone: $CHCl_3$ (1:1) showed that starting material ($R_f$=0.68) was reacted and that one lower spot had formed at $R_f$=0.47. The reaction was treated with acetone (20 ml) concentrated to dryness, taken up in acetone again (100 ml) and concentrated. The residue was taken up in acetone (100 ml) and filtered. The precipitate was washed with acetone and the filtrate was concentrated to a yellow oil. Crude product was purified on a silica gel column (5×18 cm) eluted with acetone : $CH_2Cl_2$ (1:1). Product was obtained as a white solid, 1.46 g (3.83 mmol) after drying. $^1H$ NMR showed that this material was a mixture of the 3,5 diacetate and the 2,5 diacetate. These two products were separated by recrystallization from dichloromethane and heptane with the 2,5-diacetate precipitating first. The 2,5 diacetate was obtained as white crystals 0.256 g (0.67mmol) after two recrystalizations: m.p.=210°–212° C. (uncorrected): UV $\lambda_{max}$ ($\epsilon$): pH–7.00: 279.2 nm (8,200), 248.3 nm (8,700); 0.1N HCl : 287.1 (7,800), 244.3 (6,200); 0.1N NaOH: 278.7 (8,600), 248.7 (7,900); MS(EI):m/z 381 (M+H, $C_{15}H_{19}N_5O_7$), 338 ($C_{13}H_{16}N_5O_6$), 250 ($C_{10}H_{12}N_5O_3$), 217 ($C_9H_{13}O_6$), 194 ($C_7H_8N_5O_2$), 166 ($C_6H_8N_5O$), 165 ($C_6H_7N_5O$), 157 ($C_7H_9O_4$), 139 ($C_7H_7O_3$), 135 ($C_5H_5N_5$), 43 ($C_2H_3O$); $^1$H-NMR (Me$_2$SO-d$_6$, 200 MHz): δ 7.89 (s,1H, H-8), 6.51 (br. s, 2H, NH$_2$), 6.32 (d, 1H, H-1', J=5.7 Hz), 5.98(d, 1H, 3'-OH, J=3.9 Hz), 5.18 (t, 1H, H-2', J=2.7 Hz), 4.44–4.22 (m, 3H, H-3' and 5'), 4.07–3.97 (m, 1H, H-4'), 3.94(s, 3H, Pur-OCH$_3$, 2.02 (s, 3H, C(O)CH$_3$), 1.78(s, 3H, C(O)CH$_3$; Anal. Calcd. for $C_{15}N_{19}N_5O_7 \cdot 0.40$ $CH_2Cl_2 \cdot 0.05C_7H_{16}$: Calcd: C,45.02; H,4.94; N,16.66 Found: C,44.92; H,4.92; N,16.51

L (i) 9-(2-O-Acetyl-3,5-di-O-tert-butyldimethylsilyl-β-D-arabinofuransyl)-2-amino-6-methoxy-9H-purine 2-Amino-9-(3,5-di-O-tertbutyldimethylsilyl-β-D-arabinofuransyl)-6-methoxy-9H-purine (0.5 g, 0.95 mmol) was weighed in to a flame dried 100 ml round bottom flask. 4-N,N-Dimethylaminopyridine (0.01 g, 0.09 mmol) was added and the flask was flushed with argon and sealed with a septum. Dry acetonitrile (25 ml) and triethylamine (5.0 ml) were added and the solution was cooled in an ice bath. Acetic anhydride (0.11 ml, 1.1 mmol) was added to the reaction mixture via syringe and needle. The reaction was monitored by TLC on silica gel with 1:10 acetone : $CHCl_3$. After 18 hours at ambient temperature all the starting material ($R_f$–0.20) was used up and one large product spot ($R_f$–0.51) had formed. The reaction mixture was concentrated and the residue was taken up in ethyl acetate (75 ml) and extracted with NaHCO$_3$(25 ml) and then with H$_2$O (2×25 ml). The organic layer was dried with MgSO$_4$ (anhydrous), filtered and concentrated to give a light yellow oil. The residue was purified on a silica gel column (12.5×14 cm, 230–400 mesh) eluted with acetone:CHCl$_3$ (1:4). Pure product was isolated as a white solid (0.58 g, 1.0 mmol): m.p.=74°–76° C. (uncorrected); MS(EI):m/z 568 ($C_{25}H_{46}N_5O_6Si_2$); 552 ($C_{24}H_{42}N_5O_6Si_2$), 510 ($C_{21}H_{36}N_5O_6Si_2$), 378 ($C_{15}H_{20}N_5O_5Si$), 261 ($C_{11}H_{25}O_3Si_2$), 250 ($C_{10}H_{12}N_5O_3$), 194 ($C_7H_8N_5O_2$), 166 ($C_6H_8N_5O$); $^1$H-NMR(CDCl$_3$, 200 MHz) δ 7.95 (s, 1H, H-8), 6.38 (d, 1H, H-1', J=5.6 Hz), 5.33 (t, 1H, H-2', J=5.7 Hz), 4.85 (br. s, 2H, NH$_2$), 4.58 (t,1H, H-3', J=5.8 Hz), 4.05 (s,3H, —OCH$_3$), 3.94–3.80 (m,3H, H-4' and H-5') 1.78 (s,1H,C(O)CH$_3$), 0.93 (s,9H, —SiC(CH$_3$)$_3$), 0.89 (s,9H, —SiC(CH$_3$)$_3$), 0.11–0.08 (m,12H, —Si(CH$_3$)); Anal. Calcd. for $C_{25}H_{45}N_5O_6Si_2$: Calcd: C,52.88; H,7.99; N,12.33 Found: C,52.67; H, 7.90; N,12.23

L (ii) 9-(2-O-Acetyl-5-D-arabinofuranosyl)-2-amino-6-methoxy-9H-purine

The silylated intermediate 2-amino-9-[(2-O-acetyl-3,5-di-O-tert-butyldimethylsilyl)-β-D-arabinofuranosyl]-6methoxy-9Hpurine (0.46 g, 0.8 mmol) was weighed into a RBF fitted with a stir bar and rubber septum. Tetraethylammonium fluoride (0.48 g, 3.24 mmol) was added followed by a solution of THF (40 ml) and acetic acid (0.18 ml, 3.2 mmol). The solution was cooled in an ice bath to 0°–5° C. After 48 hours at 0°–5° C., TLC in acetone : CHCl$_3$ (1:10) showed that the starting material was used up ($R_f$–0.37) and one main lower $R_f$ spot had formed ($R_f$–0.07). The reaction mixture was passed directly onto a silica gel column (230–400 mesh, 5×12 cm) and eluted with 1:1 acetone:CHCl$_3$ (300 ml) then with 5:4 acetone:CHCl$_3$ (900 ml). Pure product was obtained from the column as a white solid (0.21 g, 0.63 mmol) after drying and was shown to be the desired 2'-O-acetyl derivative: m.p.=66°–68° C. (uncorrected); $UV\lambda_{max}(\epsilon)$: pH=7.00: 279.0 nm (8,100), 247.9 nm (8,400); 0.1N HCl: 286.4(8,500), 243.4(7,000); 0.1N NaOh: 278.8 (8,700), 246.7(8,600); MS(EI): m/z 339 (M, $C_{13}H_{17}N_5O_6$), 296 ($C_{11}H_{14}N_5O_5$), 250 ($C_{10}H_{12}N_5O_3$), 194 ($C_7H_8N_5O_2$), 175 ($C_7H_{11}O_5$), 165 ($C_6H_7N_5O$); $^1$H-NMR (Me$_2$SO-d$_6$, 200 MHz): δ 7.94 (s,1H, H-2), 6.49 (br.s.2H,NH$_2$), 6.27 (d,1H, H-1', J=5.5 Hz), 5.82 (d,1H,3'-OH, J=5.1 Hz), 5.18 (t,1H, H-2', J=5.3 Hz), 5.02(t,1H,5'-OH,J=5.6 Hz), 4.33 (ddd,1H, H-3'J$_{3',3'-OH}$=5.1 Hz, J$_{2',3}$=5.3 Hz, J$_{3',4}$=5.8 Hz), 3.94 (s,3H,Pur—OCH$_3$), 3.85–3.79 (m,1H, H-4'), 3.68–3.60 (m,2H, H-5'), 1.76 (s,3H,C(O)CH$_3$); Anal. Calcd. for $C_{13}H_{17}N_5O_6 \cdot 0.40$ $CHCl_3 \cdot 0.25C_3H_6O$: Calcd: C,44.36; H,4.99; N,18.54 Found: C,44.38; H,5.27; N,18.28 m(i) 2-Amino-9-(2,3,5-tri-O-acetyl-β-D-arabinofuranosyl)-6-methoxy-9H-purine

2-Amino-9-(β-D-arabinofuranosyl)-6-methoxy-9 H-purine (1.5 g, 5.05 mmoles), triethylamine (3.06 g, 30.3 mmoles) and acetic anhydride (2.06 g, 20.2mmoles) were stirred 3 hours at room temperature in 15 mL of dry DMF under a nitrogen atmosphere. The solution was then diluted with ethyl acetate (100 mL) and the organic phase was washed with 2×100 mL portions of 10% NaHCO₃. The solvent was removed by rotary evaporation affording 2.05 g (96%) of an oil which crystallized upon standing overnight:

TLC (silica gel) chloroform:methanol (90:10) Rf=0.63; $^1$H NMR (DMSO) δ 1.86 (s,3H,OAc), 2.06 (s,3H,OAC), 2.12 (s,3H,OAc), 3.9, (s,3H,OCH₃), 4.2–4.5 (m,3H,C-4' and C-5'H), 5.4–5.5 (m,2H,C-2' and C-3'H), 6.38 (d, J=4.8 Hz, 1H, C-1'H), 6.55 (broad s, 2H, NH₂) and 7.95 (s,1H,C-8H).

m(ii) 2-Amino-9-(5-O-acetyl-β-D-arabinofuranosyl)-6-methoxy-9H-purine

A mixture of 2-amino-9-(2,3,5-tri-O-acetyl-β-D-arabinofuranosyl)-6-methoxy-9H-purine (10.0 g, 23.6 mmoles), anhydrous sodium acetate (19.4 g, 236 mmoles) and hydroxylamine hydrochloride (16.4 g, 236 mmoles) was stirred 17 hours in 200 mL of pyridine at ambient temperature. The solution was then diluted with 50 mL of acetone and most of the solvent removed by rotary evaporation.

The remaining residual oil was purified by flash column chromatography (10×75 cm, 230–400 mesh) using CHCl₃:acetone (1:1) as the eluent. Appropriate fractions were concentrated by rotary evaporation leaving a gummy semi-solid. The semi-solid was lyophillized from 100 mL of water affording a white powder: MP=138°–140° C. (uncorrected):

TLC (silica gel) chloroform:methanol (90:10) Rf=0.27; $^1$H NMR (DMSO) δ 2.03 (s,3H,OAc), 3.97 (s,3H,OCH₃), 4.1–4.4 (m,5H,C-2', C-3', C-4' and C-5'H), 5.69 (d, J=3.4 Hz, 1H,OH), 5.78 (d, J=4.2 Hz,1H,OH), 6.17 (d, J=3.6 Hz, 1H,C-1'H), 6.48 (broad s,2H,NH₂) and 7.86 (s,1H,C-8H); Anal. Calcd for $C_{13}H_{17}N_5O_6 \cdot H_2O$: Calcd: C, 43.70, H, 5.36, N, 19.60 Found: C, 43.70, H, 5.34, N, 19.52

Tablet Formulations

The following formulations A and B are prepared by wet granulation of the ingredients with a solution of povidone, followed by addition of magnesium stearate and compression.

Formulation A

|     |                         | mg/tablet | mg/tablet |
| --- | ----------------------- | --------- | --------- |
| (a) | Active Ingredient       | 250       | 250       |
| (b) | Lactose B.P.            | 210       | 26        |
| (c) | Povidone B.P.           | 15        | 9         |
| (d) | Sodium Starch Glycollate| 20        | 12        |
| (e) | Magnesium Stearate      | 5         | 3         |
|     |                         | 500       | 300       |

Formulation B

|     |                         | mg/tablet | mg/tablet |
| --- | ----------------------- | --------- | --------- |
| (a) | Active Ingredient       | 250       | 250       |
| (b) | Lactose B.P.            | 150       | —         |
| (c) | Avicel PH 101           | 60        | 26        |
| (d) | Povidone B.P.           | 15        | 9         |
| (e) | Sodium Starch Glycollate| 20        | 12        |
| (f) | Magnesium Stearate      | 5         | 3         |
|     |                         | 500       | 300       |

Formulation C

|                          | mg/tablet |
| ------------------------ | --------- |
| Active Ingredient        | 100       |
| Lactose B.P.             | 200       |
| Povidone B.P.            | 50        |
| Sodium Starch Glycollate | 5         |
| Magnesium Stearate       | 4         |
|                          | 359       |

Tablets are prepared from the foregoing ingredients (C) by wet granulation followed by compression. In an alternative preparation the Povidone B.P. may be replaced by Polyvinylpyrrolidone.

The following formulations, D and E, are prepared by direct compression of the admixed ingredients. The lactose in formulation E is of the direct compression type (Dairy Crest—"Zeparox").

Formulation D

|                         | mg/capsule |
| ----------------------- | ---------- |
| Active Ingredient       | 250        |
| Pregelatinized Starch NF25 | 250     |
|                         | 400        |

Formulation E

|                   | mg/capsule |
| ----------------- | ---------- |
| Active Ingredient | 250        |
| Lactose           | 150        |
| Avicel            | 100        |
|                   | 500        |

Formulation F (Controlled Release Formulation)

The formulation is prepared by wet granulation of the ingredients (below) with a solution of povidone followed by the addition of magnesium stearate and compression.

|     |                                                 | mg/tablet |
| --- | ----------------------------------------------- | --------- |
| (a) | Active Ingredient                               | 500       |
| (b) | Hydroxypropylmethylcellulose (Methocel K4M Premium) | 112   |
| (c) | Lactose B.P.                                    | 53        |
| (d) | Povidone B.P.                                   | 28        |
| (e) | Magnesium Stearate                              | 7         |
|     |                                                 | 700       |

Drug release takes place over a period of about 6–8 hours and is complete after 12 hours.

Capsule Formulations

Formulation A

A capsule formulation is prepared by admixing the ingredients of Formulation D in Example 12 above and filling into a two-part hard gelatin capsule. Formulation B (infra) is prepared in a similar manner.

Formulation B

|     |                         | mg/capsule |
| --- | ----------------------- | ---------- |
| (a) | Active ingredient       | 250        |
| (b) | Lactose B.P.            | 143        |
| (c) | Sodium Starch Glycollate| 25         |
| (d) | Magnesium Stearate      | 2          |
|     |                         | 420        |

Formulation C

|     |                   | mg/capsule |
| --- | ----------------- | ---------- |
| (a) | Active ingredient | 250        |
| (b) | Macrogol 4000 B.P.| 350        |
|     |                   | 600        |

Capsules are prepared by melting the Macrogol 4000 BP, dispersing the active ingredient in the melt and filling the melt into a two-part hard gelatin capsule.

Formulation D

|                   | mg/capsule |
| ----------------- | ---------- |
| Active ingredient | 250        |
| Lecithin          | 100        |
| Arachis Oil       | 100        |
|                   | 450        |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronization of the extrudate and drying. The dried pellets are then coated with release-controlling membrane (d) and filled into a two-piece, hard gelatin capsule.

|     |                       | mg/capsule |
| --- | --------------------- | ---------- |
| (a) | Active Ingredient     | 250        |
| (b) | Microcrystalline Cellulose | 125   |
| (c) | Lactose B.P.          | 125        |
| (d) | Ethyl Cellulose       | 13         |
|     |                       | 513        |

Ophthalmic Solution

| Active Ingredient              |       | 0.5     |
| ------------------------------ | ----- | ------- |
| Sodium chloride, analytical grade |   | 0.9 g   |
| Thiomersal                     |       | 0.001 g |
| Purified water                 | to    | 100 ml  |
| pH adjusted                    | to    | 7.5     |

Injectable Formulation

| Active Ingredient                         |     | 0.200 g |
| ----------------------------------------- | --- | ------- |
| Sterile, pyrogen free phosphate buffer (pH 7.2) | to | 10 ml   |

The active ingredient is dissolved in most of the phosphate buffer (35°–40° C.), then made up to volume and filtered through a sterile micropore filter into a sterile 10 ml amber glass via (type 1) and sealed with sterile closures and overseals.

Intramuscular Injection

| Active Ingredient  |         | 0.20 g  |
| ------------------ | ------- | ------- |
| Benzyl Alcohol     |         | 0.10 g  |
| Glycofurol 75      |         | 1.45 g  |
| Water for Injection| q.s. to | 3.00 mo |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

Syrup Suspension

| Active Ingredient        |         | 0.25 g    |
| ------------------------ | ------- | --------- |
| Sorbitol Solution        |         | 1.50 g    |
| Glycerol                 |         | 2.00 g    |
| Dispersible Cellulose    |         | 0.075 g   |
| Sodium Benzoate          |         | 0.005 g   |
| Flavor, Peach 17.42.3169 |         | 0.0125 ml |
| Purified Water           | q.s. to | 5.00 ml   |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Suppository

|                                              | mg/suppository |
| -------------------------------------------- | -------------- |
| Active ingredient (63 μm)*                   | 250            |
| Hard Fat, 3P (Witepsol H15 - Dynamit Nobel)  | 1700           |
|                                              | 1950           |

*The active ingredient is used as a powder wherein at least 90% of the particles are of 63 μm diameter or less.

One-fifth of the Witepsol H15 is melted in a steam-jacketed at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H25 is added to the suspension and stirred to ensure a homogenous mix. The entire suspension is passed through a 250 μm stainless steel screen and, with continuous stirring, is allowed to cool to 45° C. At a temperature of 38° C. to 40° C., 202 g of the mixture is filled into suitable plastic molds. The suppositories are allowed to cool to room temperature.

Pessaries

|                            | mg/pessary |
| -------------------------- | ---------- |
| Active ingredient (63 μm)* | 250        |
| Anhydrate Dextrose         | 380        |
| Potato Starch              | 363        |
| Magnesium Stearate         | 7          |
|                            | 1000       |

The above ingredients are mixed directly and pessaries prepared by direct compression of the resulting mixture.

Selective Inhibition of T Cell Growth

The compounds of the invention were tested for inhibition of the growth of T cells (Molt 4) compared to B cells (IM9) by the method of Averett, D., Journal of Virological Methods, 23, (1989), 263–276.

2-Amino-6-methoxy-9-(β-D-arabinofuranosyl)-9H-purine (compound 1) selectively inhibits the growth of a human T-cell line (Molt 4) in contrast to a human B-cell line (IM9). These data are compared with selective inhibition of ara G.

|  | $IC_{50}$ μM (% of Control growth) | |
|---|---|---|
| Compound | Molt 4 cells | IM9 cells |
| 1 | 0.8 ± 0.1 | >10 (85%) |
| araG | 1.4 ± 0.08 | >10 (84%) |

Bioavailability of Ara G

AraG and compounds of the invention were administered orally to Cynomolgus monkeys which had been fasted for eight hours. Each compound was given to two monkeys. The dosage was 94 μmol/kg which is equivalent to 27 mg/kg araG. Blood samples were taken over the following 24 hours, and urine was collected over the same 24 hours. Concentrations of araG in plasma extracts and urine were determined by reverse phase HPLC.

| | Solubilities and Bioavailabilty of araG | | |
|---|---|---|---|
| | | Plasma | Urine |
| Compound | Solubility (mM) in PBS* at 25° C. | araG Peak Level (μM) | AUC** 0.7 hrs | % Recovered as araG |
| araG | 4 | 6 | 20.8 | 3.9 |
| | | 4.6 | 21.1 | 4.2 |
| Example 1b | 92 | 19.8 | 78 | 26.3 |
| | | 21.6 | 83 | 33.6 |
| Example 2j | 38 | 18.7 | 86.9 | 25.8 |
| | | 15.7 | 83.5 | 13.5 |

*Phosphate buffered saline
**Area under curve (μM × hrs)

We claim:

1. The method of treating a mammal having lymphocytic leukemia which comprises administering to said mammal an effective treatment amount of the compound 2-amino-6-methoxy-9-(β-D-arabinofuranosyl)-9H-purine.

2. The method of treating a mammal having lymphoma which comprises administering to said mammal an effective treatment amount of the compound 2-amino-6-methoxy-9-(β-D-arabinofuranosyl)-9H-purine.

3. A method for the treatment of mammalian tumors susceptible to inhibition of T-cell growth, said method comprising administering to a mammal having said tumor an effective T-cell growth inhibiting amount of a compound of formula (I)

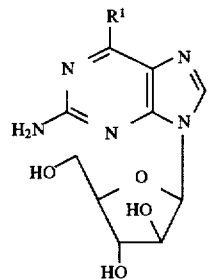

wherein:
$R^1$ is methoxy; or
a pharmaceutically acceptable ester or salt thereof.

4. A method for the treatment of T-cell lymphoproliferative disorders in a mammal, said method comprising administering to said mammal an effective T-cell lymphoproliferative disorder treatment amount of a compound of formula (I)

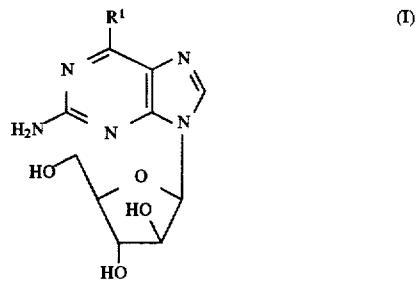

$R^1$ is methoxy; or a pharmaceutically acceptable ester or salt thereof.

5. A method according to claim 4, wherein the T-cell lymphoproliferative disorder is an autoimmune disease.

6. A method according to claim 5, wherein the autoimmune disease is arthritis.

7. A method according to claim 5, wherein the autoimmune disease is insulin dependent diabetes mellitus.

8. A method for the treatment of mammalian tumors susceptible to inhibition of T-cell growth, said method comprising administering to a mammal having said tumor an effective T-cell growth inhibiting amount of 2-amino-6-methoxy-9-(β-D-arabinofuranosyl)-9H-purine or a pharmaceutically acceptable ester or salt thereof.

9. The method of claims 8 wherein said ester is (5-O-acetyl-β-D-arabinofuranosyl)-2-amino-6-methoxy-9-9H-purine.

10. A method for the treatment of T-cell lymphoproliferative disorders in a mammal, said method comprising administering to said mammal an effective T-cell lymphoproliferative disorder treatment amount of 2-amino-6-methoxy-9-(β-D-arabinofuranosyl)-9H-purine or a pharmaceutically acceptable ester or salt thereof.

11. The method of claim 10 wherein said ester is (5-O-acetyl-β-D-arabinofuranosyl)-2-amino-6-methoxy-9-9H-purine.

* * * * *